United States Patent
Zubiate et al.

(10) Patent No.: US 8,919,710 B2
(45) Date of Patent: Dec. 30, 2014

(54) APPARATUS FOR POSITIONING A DEVICE

(71) Applicant: Carnegie Mellon University, Pittsburgh, PA (US)

(72) Inventors: Brett Zubiate, Duxbury, MA (US); Sarjoun Skaff, Pittsburgh, PA (US); Amir Degani, Pittsburgh, PA (US); Howie Choset, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 0 days.

(21) Appl. No.: 13/804,990

(22) Filed: Mar. 14, 2013

(65) Prior Publication Data

US 2013/0228663 A1 Sep. 5, 2013

Related U.S. Application Data

(60) Division of application No. 13/089,922, filed on Apr. 19, 2011, now Pat. No. 8,444,096, which is a continuation of application No. 11/876,304, filed on Oct. 22, 2007, now Pat. No. 7,946,546.

(60) Provisional application No. 60/862,310, filed on Oct. 20, 2006.

(51) Int. Cl.
- *A47F 5/00* (2006.01)
- *A47F 7/00* (2006.01)
- *F16M 11/00* (2006.01)
- *F16M 13/00* (2006.01)

(52) U.S. Cl.
USPC .................. 248/122.1; 248/121; 248/181.1

(58) Field of Classification Search
None
See application file for complete search history.

(56) References Cited

U.S. PATENT DOCUMENTS

| | | | |
|---|---|---|---|
| 992,509 | A | 5/1911 | Kobzy |
| 2,238,660 | A | 4/1941 | Santora |
| 4,364,535 | A | 12/1982 | Itoh et al. |
| 4,548,373 | A | 10/1985 | Komura |
| 4,556,626 | A | 12/1985 | Speigel |
| 4,884,916 | A | 12/1989 | Johnson, III |
| 4,946,122 | A | 8/1990 | Ramsey et al. |
| 5,253,832 | A | 10/1993 | Bolas et al. |
| 5,571,072 | A | 11/1996 | Kronner |
| 5,597,146 | A | 1/1997 | Putman |
| 5,615,856 | A | 4/1997 | Simington |
| 5,695,501 | A | 12/1997 | Carol et al. |
| 5,957,423 | A | 9/1999 | Kronner |
| 5,957,832 | A | 9/1999 | Taylor et al. |
| 6,004,016 | A | 12/1999 | Spector |
| 6,090,114 | A | 7/2000 | Matsuno et al. |
| 6,540,188 | B2 | 4/2003 | Jenkins et al. |
| 6,547,782 | B1 * | 4/2003 | Taylor .................. 606/14 |
| 6,808,493 | B1 | 10/2004 | Bookwalter et al. |
| 6,817,641 | B1 | 11/2004 | Singleton, Jr. |
| 6,953,222 | B2 | 10/2005 | Larrick et al. |
| 7,056,287 | B2 | 6/2006 | Taylor et al. |
| 7,445,184 | B1 | 11/2008 | Johnson |

(Continued)

*Primary Examiner* — Amy J Sterling
(74) *Attorney, Agent, or Firm* — Fox Rothschild LLP

(57) ABSTRACT

An apparatus for positioning a device. The apparatus includes a coupling member, a first arm, a second arm, and a sloped support member. The coupling member defines a first opening and a second opening. The first arm passes through the first opening, and the coupling member is movably connected to the first arm. The second arm passes through the second opening. The sloped support member is releasably connected to the second arm. The apparatus has at least five degrees of freedom.

15 Claims, 35 Drawing Sheets

(56) References Cited

U.S. PATENT DOCUMENTS

| | | |
|---|---|---|
| 7,947,000 B2 | 5/2011 | Vargas et al. |
| 8,265,734 B2 * | 9/2012 | Ishikawa et al. .............. 600/476 |
| 2002/0022764 A1 | 2/2002 | Smith et al. |
| 2003/0045768 A1 * | 3/2003 | Hirooka et al. .................. 600/2 |
| 2005/0234293 A1 | 10/2005 | Yamamoto et al. |
| 2006/0063977 A1 | 3/2006 | Sharratt et al. |
| 2007/0089557 A1 * | 4/2007 | Solomon et al. ........... 74/490.01 |
| 2009/0054765 A1 | 2/2009 | Namii et al. |
| 2011/0118545 A1 * | 5/2011 | Williams et al. .............. 600/104 |

* cited by examiner

APPARATUS FOR POSITIONING A DEVICE

CROSS REFERENCE TO RELATED APPLICATION

This application is a divisional of and claims priority to U.S. patent application Ser. No. 13/089,922 filed Apr. 19, 2011, which is a continuation of and claims priority to U.S. patent application Ser. No. 11/876,304, filed Oct. 22, 2007, now U.S. Pat. No. 7,946,546, which claims the priority benefit of U.S. Provisional Patent Application No. 60/862,310, filed on Oct. 20, 2006.

BACKGROUND

This application discloses an invention that is related, generally and in various embodiments, to an apparatus for positioning a device.

In conventional surgery, surgical devices are often supported by the hands of one or more surgeons or assistants positioned proximate a patient. For applications involving robotic surgery, surgical devices are generally supported by one or more robotic arms. In many cases, the number, size and positioning of such robotic arms tend to interfere with the desired movements of the surgeons and/or assistants proximate a patient.

SUMMARY

In one general respect, this application discloses an apparatus for positioning a device. According to various embodiments, the apparatus includes a coupling member, a first arm, a second arm, and a sloped support member. The coupling member defines a first opening and a second opening. The first arm passes through the first opening, and the coupling member is movably connected to the first arm. The second arm passes through the second opening. The sloped support member is releasably connected to the second arm. The apparatus has at least five degrees of freedom.

DESCRIPTION OF DRAWINGS

Various embodiments of the invention are described herein by way of example in conjunction with the following figures.

DETAILED DESCRIPTION

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

According to various embodiments, the apparatus may be utilized to position a variety of different devices. For example, the apparatus may be utilized to position a device such as a feeder that may be utilized to insert or extract a multi-linked device into or from a patient. For ease of explanation purposes, the apparatus will be described in the context of its use with a feeder and various embodiments of the steerable multi-linked device described in FIGS. 1-11. However, one skilled in the art will appreciate that the apparatus may be utilized to position other types of devices.

Figure 1A:
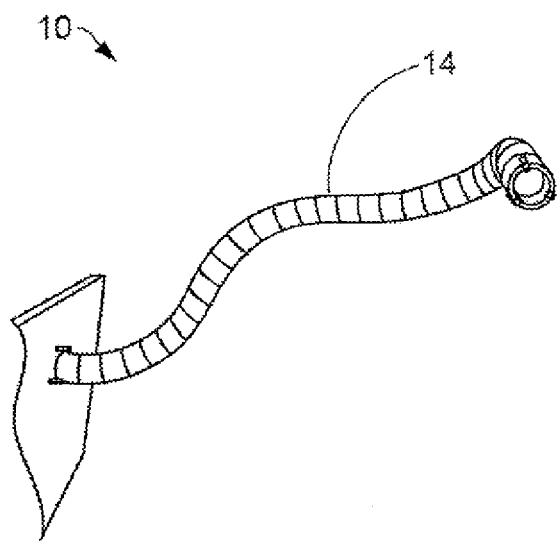
FIGS. 1A and 1B illustrate various embodiments of a steerable multi-linked device.
Figure 1B:
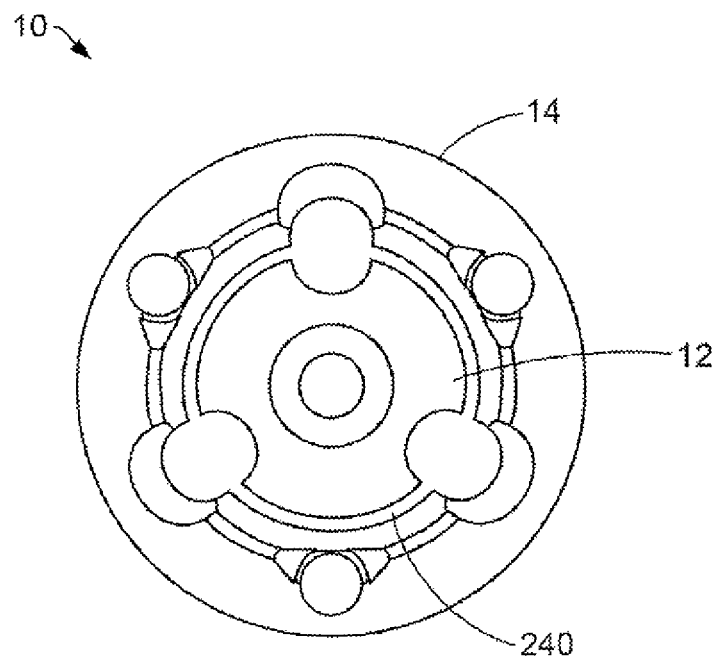

FIGS. 1A and 1B illustrate various embodiments of a steerable multi-linked device 10. Various embodiments of the device 10 may be utilized for medical procedures (e.g., minimally invasive procedures), for surveillance applications, for inspection applications, for search and rescue applications, etc. For purposes of clarity only, the utility of the device 10 will be described hereinbelow in the context of its applicability to medical procedures. However, a person skilled in the art will appreciate that the device 10 can be utilized in a variety of different applications.

The device 10 includes a first mechanism 12 and a second mechanism 14. According to various embodiments, the second mechanism 14 is structured and arranged to receive and surround the first mechanism 12 as shown in FIG. 1B. For such embodiments, the first mechanism 12 may be considered the inner mechanism or the core mechanism, and the second mechanism 14 may be considered the outer mechanism or the sleeve mechanism. According to other embodiments, the first and second mechanisms 12, 14 may be structured and arranged to have a relationship other than a concentric relationship. For example, one skilled in the art will appreciate that, according to various embodiments, the first and second mechanisms 12, 14 may be structured and arranged to operate in a side-by-side arrangement, where the first mechanism 12 operates adjacent to the second mechanism 14. As described in more detail hereinbelow, the first mechanism 12 may operate in either a rigid mode or a limp mode, the second mechanism 14 may operate in either a rigid mode or a limp mode, and the first and second mechanisms 12, 14 may operate independent of one another. Both the first mechanism 12 and the second mechanism 14 may be steerable mechanisms. Accordingly, it will be appreciated that the device 10 may be utilized to navigate a luminal space as well as any three-dimensional path within an intracavity space. The device 10 may also comprise a first cable 16, a second cable 18, a third cable 20, and a fourth cable 22. The first, second and third cables 16, 18, 20 may be considered steering cables, and the fourth cable 22 may be considered a tensioning cable.

Figure 2:
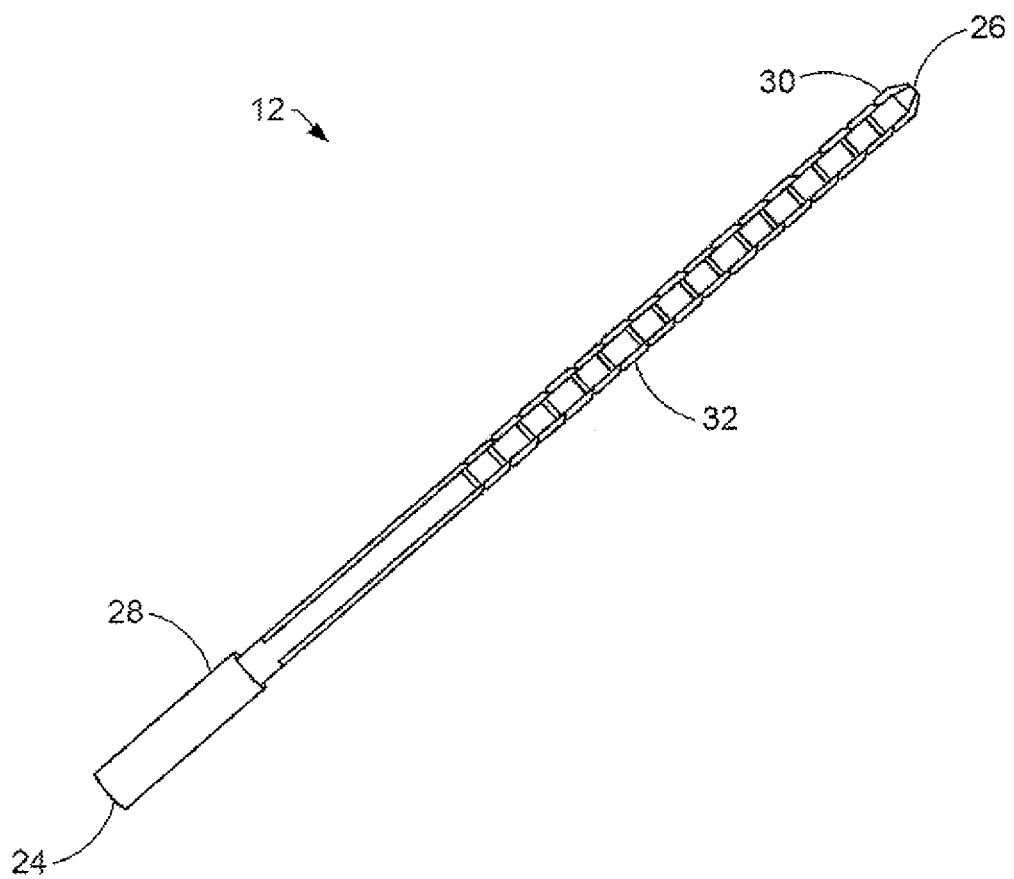
FIG. 2 illustrates various embodiments of a core mechanism of the device of FIGS. 1A and 1B.

FIG. 2 illustrates various embodiments of the first mechanism 12 of the device 10. The first mechanism 12 is a multi-linked mechanism and includes a first end 24 and a second end 26. The first end 24 may be considered the proximal end and the second end 26 may be considered the distal end. The first mechanism 12 includes a first link 28, a second link 30, and any number of intermediate links 32 between the first and second links 28, 30. The first link 28 may be considered the proximal link, and the second link 30 may be considered the distal link.

Figure 3A:
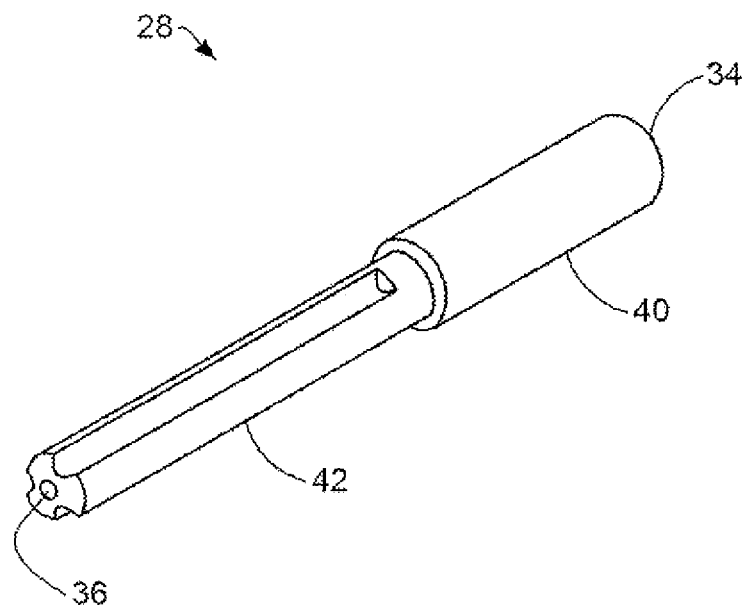
FIGS. 3A-3C illustrate various embodiments of a proximal link of the core mechanism.
Figure 3B:
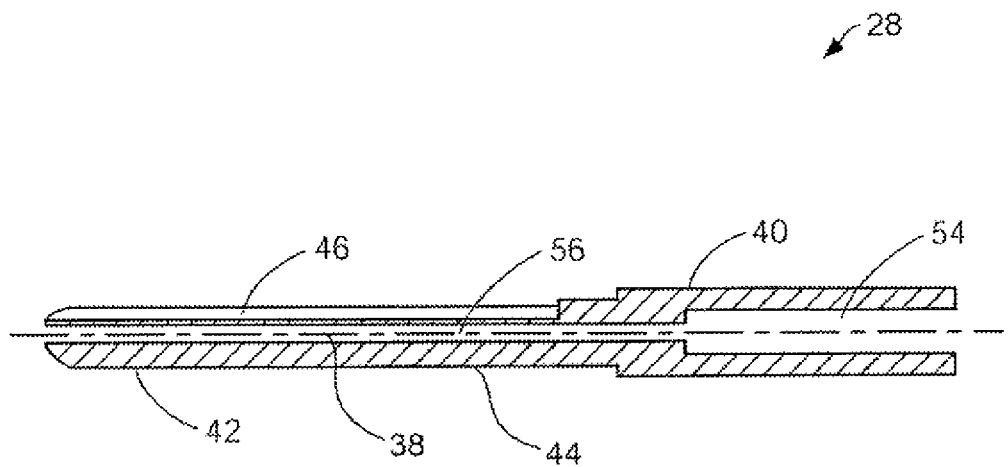
Figure 3C:
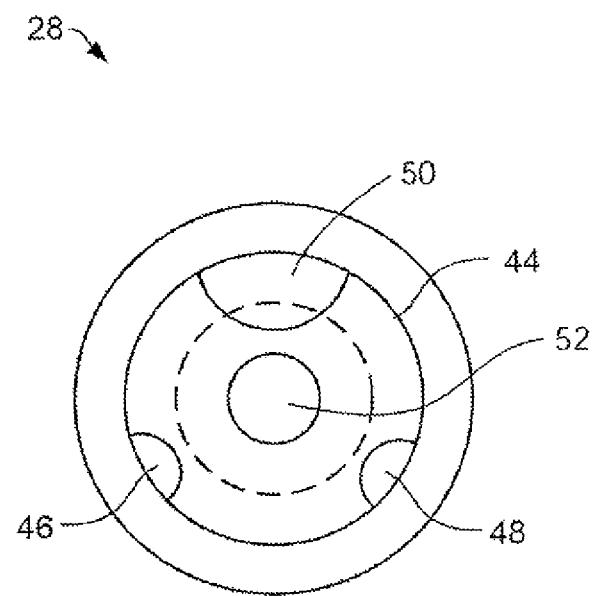

FIGS. 3A-3C illustrate various embodiments of the first link 28 (inner proximal link) of the first mechanism 12. The first link 28 includes a first end 34 and a second end 36, and defines a longitudinal axis 38 that passes through the center of the first end 34 and the center of the second end 36 as shown in FIG. 3B. The first link 28 may be fabricated from any suitable material. According to various embodiments, the first link 28 is fabricated from a fiber reinforced material such as, for example, G10/FR4 Garolite®. The first link 28 has a generally cylindrical shaped exterior and is described in more detail hereinbelow.

The first link 28 includes a first portion 40 and a second portion 42. The first portion 40 may be considered the proximal portion and the second portion 42 may be considered the distal portion. The first portion 40 may be fabricated integral with the second portion 42. The first portion 40 has a cylindrical shaped exterior, and extends from the first end 34 of the first link 28 toward the second end 36 of the first link 28. According to various embodiments, the diameter of the first portion 40 is on the order of approximately 6.35 millimeters.

The second portion 42 has a generally cylindrically shaped exterior. The second portion 42 has a cylindrically shaped exterior where it contacts the first portion 40, and tapers toward the second end 36 of the first link 28. The second portion 42 may be shaped in the form of a generally segmented hemisphere at the second end 36 of the first link 28. According to various embodiments, the diameter of the second portion 42 is on the order of approximately 4.75 millimeters where it contacts the first portion 40.

The second portion 42 includes a first surface 44. The first surface 44 may be considered the outer surface of the second portion 42. The second portion 42 defines a first groove 46 parallel to the longitudinal axis 38 along the first surface 44, a second groove 48 parallel to the longitudinal axis 38 along the first surface 44, and a third groove 50 parallel to the longitudinal axis 38 along the first surface 44. Each of the first, second and third grooves 46, 48, 50 extend along the first surface 44 toward the second end 36 of the first link 28. The first, second and third grooves 46, 48, 50 may be semi-tubular shaped and may be evenly spaced about the first surface 44 of the second portion 42 of the first link 28 as shown in FIG. 3C. According to various embodiments, the first, second, and third grooves 46, 48, 50 may be configured in the shape of a segmented cylinder. The size of each of the grooves 46, 48, 50 may identical to one another or may be different from one another. For example, according to various embodiments, the first and second grooves 46, 48 are configured as segments of a cylinder having a diameter on the order of approximately 1.25 millimeters, and the third groove 50 is configured as a segment of a cylinder having a diameter on the order of approximately 2.50 millimeters. The length of the first link 28 may be on the order of approximately 65 millimeters. However, one skilled in the art will appreciate that the length of the first link 28 can vary based on the application.

The first link 28 also defines a passage 52 extending from the first end 34 to the second end 36 along the longitudinal axis 38 as shown in FIG. 3B. The passage 52 is of a size sufficient to allow the fourth cable 22 to pass therethrough. According to various embodiments, the passage 52 is generally configured as a complex shape that includes a combination of a first cylinder 54 that extends from the first end 34 toward the second end 36, and a second cylinder 56 that extends from the first cylinder 54 toward the second end 36. The diameter of the first cylinder 54 is larger than the diameter of the second cylinder 56. For example, according to various embodiments, the first cylinder 54 has a diameter on the order of approximately 3.20 millimeters and the second cylinder 56 has a diameter on the order of approximately 1.50 millimeters.

Figure 4A:
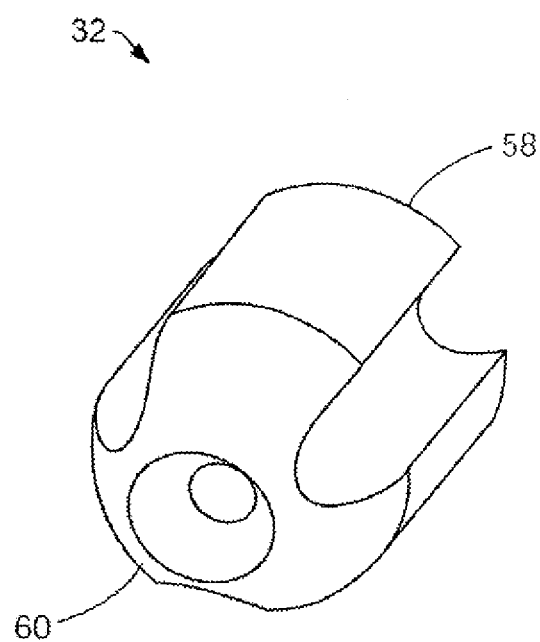
FIGS. 4A-4C illustrate various embodiments of an intermediate link of the core mechanism.
Figure 4B:
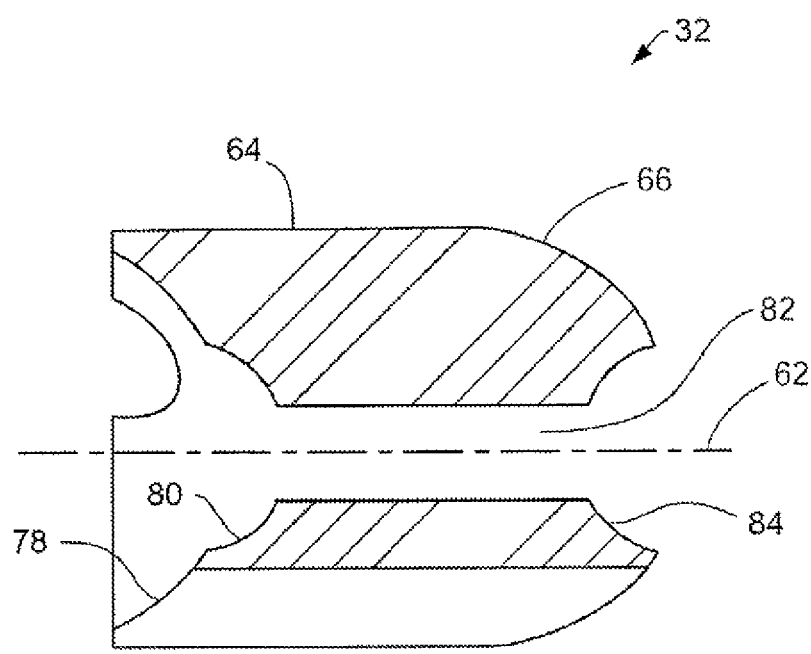
Figure 4C:
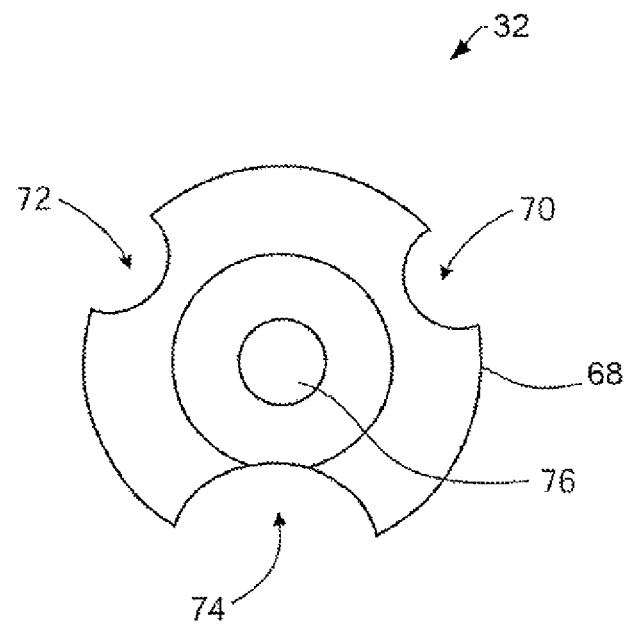

FIGS. 4A-4C illustrate various embodiments of one of the intermediate links 32 (inner intermediate link) of the first mechanism 12. The intermediate link 32 is representative of the other intermediate links 32. The intermediate link 32 includes a first end 58 and a second end 60, and defines a longitudinal axis 62 that passes through the center of the first end 58 and the center of the second end 60 as shown in FIG. 4B. The intermediate link 32 may be fabricated from any suitable material. According to various embodiments, the intermediate link 32 is fabricated from a fiber reinforced material such as, for example, G10/FR4 Garolite®. The intermediate link 32 has a generally bullet-shaped exterior and is described in more detail hereinbelow.

The intermediate link 32 includes a first portion 64 and a second portion 66. The first portion 64 may be considered the proximal portion and the second portion 66 may be considered the distal portion. The first portion 64 may be fabricated integral with the second portion 66. The first portion 64 has a generally cylindrical shaped exterior, and extends from the first end 58 of the intermediate link 32 toward the second end 60 of the intermediate link 32. According to various embodiments, the second portion 66 has a generally cylindrically shaped exterior where it contacts the first portion 64, and tapers toward the second end 60 of the intermediate link 32. The exterior of the second portion 66 is configured in the form of a generally segmented hemisphere. According to various embodiments, the diameter of the intermediate link 32 is on the order of approximately 4.75 millimeters at the first end 58 thereof. The length of the intermediate link 32 may be on the order of approximately 5.85 millimeters. However, one skilled in the art will appreciate that the length of the intermediate link 32 can vary based on the application.

The intermediate link 32 also includes a first surface 68 that extends from the first end 58 of the intermediate link 32 to the second end 60 of the intermediate link 32. The first surface 68 may be considered the outer surface of the intermediate link 32. The intermediate link 32 also defines a first groove 70 parallel to the longitudinal axis 62 along the first surface 68, a second groove 72 parallel to the longitudinal axis 62 along the first surface 68, and a third groove 74 parallel to the longitudinal axis 62 along the first surface 68. Each of the first, second and third grooves 70, 72, 74 extend along the first surface 68 from the first end 58 of the intermediate link 32 toward the second end 60 of the intermediate link 32. The first, second and third grooves 70, 72, 74 may be semi-tubular shaped and may be evenly spaced about the first surface 68 of the intermediate link 32 as shown in FIG. 4C. According to various embodiments, the first, second, and third grooves 70, 72, 74 may be configured in the shape of a segmented cylinder. The size of each of the grooves 70, 72, 74 may identical to one another or may be different from one another. For example, according to various embodiments, the first and second grooves 70, 72 are configured as segments of a cylinder having a diameter on the order of approximately 1.75 millimeters at the first end 58 of the intermediate link 32, and the third groove 74 is configured as a segment of a cylinder having a diameter on the order of approximately 2.50 millimeters at the first end 58 of the intermediate link 32. The first, second and third grooves 70, 72, 74 are each configured to receive and partially surround any of a variety of tools or instruments (e.g., ablation tools) which may pass from the first end 24 of the multi-linked device 10 to the second end 26 of the multi-linked device 10.

The intermediate link 32 also defines a passage 76 extending from the first end 58 to the second end 60 along the longitudinal axis 62 as shown in FIG. 4B. The passage 76 is of a size sufficient to allow the fourth cable 22 to pass therethrough. According to various embodiments, the passage 76 is generally configured as a complex shape that includes a combination of a first segmented hemisphere 78 that extends from the first end 58 toward the second end 60, a second segmented hemisphere 80 that extends from the first segmented hemisphere 78 toward the second end 60, a cylinder 82 that extends from the second segmented hemisphere 80 toward the second end 60, and a third segmented hemisphere 84 that extends from the cylinder 82 to the second end 60 of the intermediate link 32. According to various embodiments, the first segmented hemisphere 78 represents a portion of a sphere having a diameter on the order of approximately 4.75 millimeters, the second segmented hemisphere 80 represents a portion of a sphere having a diameter on the order of approximately 2.25 millimeters, the cylinder 82 has a diameter on the order of approximately 1.0 millimeter, and the third segmented hemisphere 84 represents a portion of a sphere having a diameter on the order of approximately 2.25 millimeters.

The first segmented hemisphere 78 of the passage 76 is configured to receive the second end 36 of the first link 28 when the first link 28 is coupled to the intermediate link 32. Similarly, for a given intermediate link 32, the first segmented hemisphere 78 of the passage 76 is configured to receive the second end 60 of another intermediate link 32 when the other intermediate link 32 is coupled to the given intermediate link 32. The third segmented hemisphere 84 may serve to reduce the pinching or binding of the fourth cable 22 when one intermediate link 32 moves relative to an adjacent intermediate link 32 coupled thereto. Similarly, when the second link 30 is coupled to a given intermediate link 32, the third segmented hemisphere 84 may serve to reduce the pinching or binding of the fourth cable 22 when the second link 30 moves relative to the given intermediate link 32.

With the above described structure, the first link 28 may be coupled to the intermediate link 32 by seating the second end 36 of the first link 28 in the first segmented hemisphere 78 of the passage 76 of the intermediate link 32. As the convex configuration of the second end 36 of the first link 28 generally corresponds with the concave configuration of the first segmented hemisphere 78 of the passage 76 of the intermediate link 32, the first link 28 may be coupled to the intermediate link 32 such that the longitudinal axis 38 and the first, second and third grooves 46, 48, 50 of the first link 28 are respectively aligned with the longitudinal axis 62 and the first, second and third grooves 70, 72, 74 of the intermediate link 32. The intermediate link 32 may be moved relative to the first link 28 such that the longitudinal axis 62 of the intermediate link 32 is not aligned with the longitudinal axis 38 of the first link 28. According to various embodiments, the configuration of the first link 28 and the intermediate link 32 allows for the intermediate link 32 to be moved relative to the first link 28 coupled thereto such that the longitudinal axis 38 of the first link 28 and the longitudinal axis 62 of the intermediate link 32 are up to approximately 25° out of alignment with one another. Similarly, one intermediate link 32 may be coupled to another intermediate link 32, and so on, by seating the second end 60 of one intermediate link 32 in the first segmented hemisphere 78 of the passage 76 of another intermediate link 32. As the convex configuration of the second end 60 of the intermediate link 32 generally corresponds with the concave configuration of the first segmented hemisphere 78 of the passage 76 of the intermediate link 32, the intermediate links 32 may be coupled such that the respective longitudinal axes 62 and the respective first, second and third grooves 46, 48, 50 of the intermediate links 32 are aligned. The coupled intermediate links 32 may be moved relative to one another such that the respective longitudinal axes 62 of the coupled intermediate links 32 are not aligned. According to various embodiments, the configuration of the coupled intermediate links 32 allows for one intermediate link 32 to be moved relative to an adjacent intermediate link 32 coupled thereto such that the respective longitudinal axes 62 are up to approximately 25° out of alignment with one another.

Figure 5A:
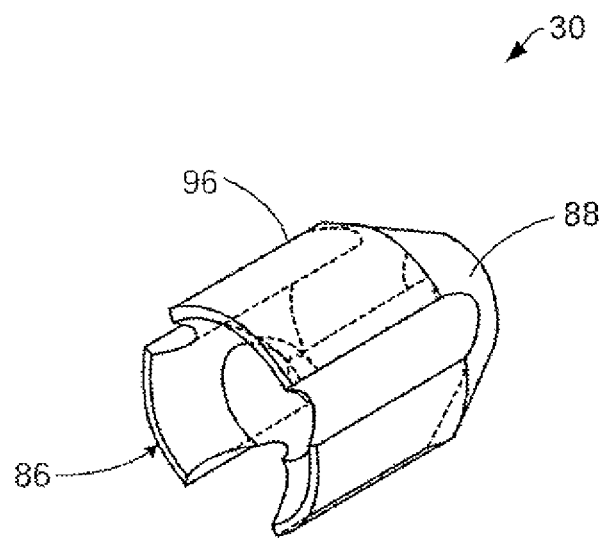
FIGS. 5A-5C illustrate various embodiments of a distal link of the core mechanism.
Figure 5B:
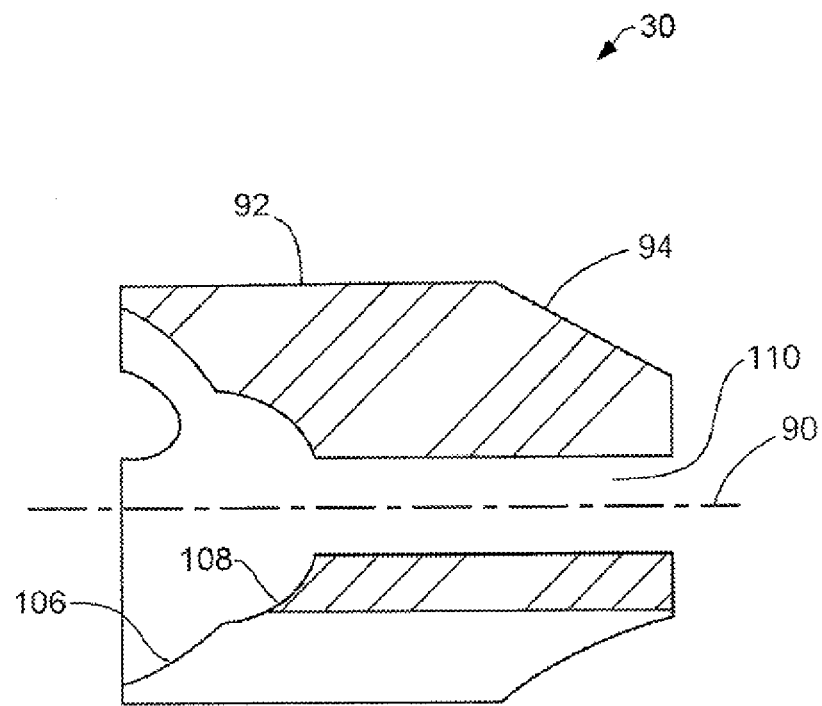
Figure 5C:
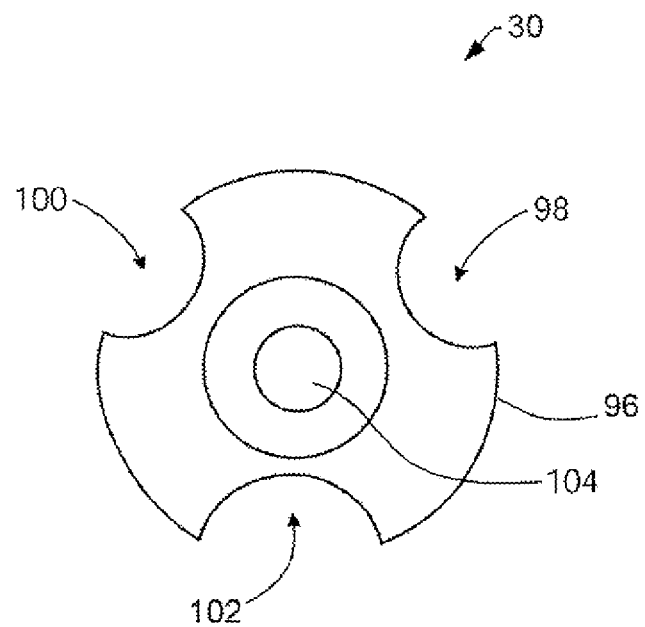

FIGS. 5A-5C illustrate various embodiments of the second link 30 (inner distal link) of the first mechanism 12. The second link 30 includes a first end 86 and a second end 88, and defines a longitudinal axis 90 that passes through the center of the first end 86 and the center of the second end 88 as shown in FIG. 5B. The second link 30 may be fabricated from any suitable material. According to various embodiments, the second link 30 is fabricated from a thermoplastic material such as, for example, Delrin®.

The second link 30 includes a first portion 92 and a second portion 94. The first portion 92 may be considered the proximal portion and the second portion 94 may be considered the distal portion. The first portion 92 may be fabricated integral with the second portion 94. The first portion 92 has a generally cylindrical shaped exterior, and extends from the first end 86 of the second link 30 toward the second end 88 of the second link 30. According to various embodiments, the second portion 94 has a generally cylindrically shaped exterior where it contacts the first portion 92, and tapers toward the second end 88 of the second link 30. The exterior of the second portion 64 is configured in the form of a generally segmented cone. According to various embodiments, the diameter of the second link 30 is on the order of approximately 4.75 millimeters at the first end 86 thereof, and the taper of the second portion 94 is at an angle of approximately 30° relative to the exterior of the first portion 92. The length of the second link 30 may be on the order of approximately 5.90 millimeters. However, one skilled in the art will appreciate that the length of the second link 30 can vary based on the application.

The second link 30 also includes a first surface 96 that extends from the first end 86 of the second link 30 to the second end 88 of the second link 30. The first surface 96 may be considered the outer surface of the second link 30. The second link 30 also defines a first groove 98 parallel to the longitudinal axis 90 along the first surface 96, a second groove 100 parallel to the longitudinal axis 90 along the first surface 96, and a third groove 102 parallel to the longitudinal axis 90 along the first surface 96. Each of the first, second and third grooves 98, 100, 102 extend along the first surface 96 from the first end 86 of the second link 30 toward the second end 88 of the second link 30. The first, second and third grooves 98, 100, 102 may be semi-tubular shaped and may be evenly spaced about the first surface 96 of the second link 30 as shown in FIG. 5C. According to various embodiments, the first, second, and third grooves 98, 100, 102 may be configured in the shape of a segmented cylinder. The size of each of the grooves 98, 100, 102 may identical to one another or may be different from one another. For example, according to various embodiments, the first and second grooves 98, 100 are configured as segments of a cylinder having a diameter on the order of approximately 1.25 millimeters at the first end 86 of the second link 30, and the third groove 102 is configured as a segment of a cylinder having a diameter on the order of approximately 2.50 millimeters at the first end 86 of the second link 30. The first, second and third grooves 98, 100, 102 are each configured to receive and partially surround any of a variety of tools or instruments (e.g., ablation tools) which may pass from the first end 24 of the multi-linked device 10 to the second end 26 of the multi-linked device 10.

The second link 30 also defines a passage 104 extending from the first end 86 to the second end 88 along the longitudinal axis 90 as shown in FIG. 5B. The passage 104 is of a size sufficient to allow the fourth cable 22 to pass therethrough. According to various embodiments, the passage 104 is generally configured as a complex shape that includes a combination of a first segmented hemisphere 106 that extends from the first end 86 toward the second end 88, a second segmented hemisphere 108 that extends from the first segmented hemisphere 106 toward the second end 88, and a cylinder 110 that extends from the second segmented hemisphere 108 to the second end 88 of the second link 30. According to various embodiments, the first segmented hemisphere 106 represents a portion of a sphere having a diameter on the order of approximately 4.75 millimeters, the second segmented hemisphere 108 represents a portion of a sphere having a diameter on the order of approximately 2.50 millimeters, and the cylinder 110 has a diameter on the order of approximately 1.0 millimeter. The first segmented hemisphere 106 of the passage 104 is configured to receive the second end 60 of an intermediate link 32 when the intermediate link 32 is coupled to the second link 30.

With the above described structure, an intermediate link 32 may be coupled to the second link 30 by seating the second end 60 of the intermediate link 32 in the first segmented hemisphere 106 of the passage 104 of the second link 30. As the convex configuration of the second end 60 of the intermediate link 32 generally corresponds with the concave configuration of the first segmented hemisphere 106 of the passage 104 of the second link 30, the intermediate link 32 may be coupled to the second link 30 such that the longitudinal axis 62 and the first, second and third grooves 70, 72, 74 of the intermediate link 32 are respectively aligned with the longitudinal axis 90 and the first, second and third grooves 98, 100, 102 of the second link 30. The second link 30 may be moved relative to the intermediate link 32 coupled thereto such that the respective longitudinal axes 62, 90 are not aligned. According to various embodiments, the configuration of the second link 30 allows for an intermediate link 32 coupled thereto to be moved relative to the second link 30 such that the respective longitudinal axes 62, 90 are up to approximately 25° out of alignment with one another.

Figure 6:
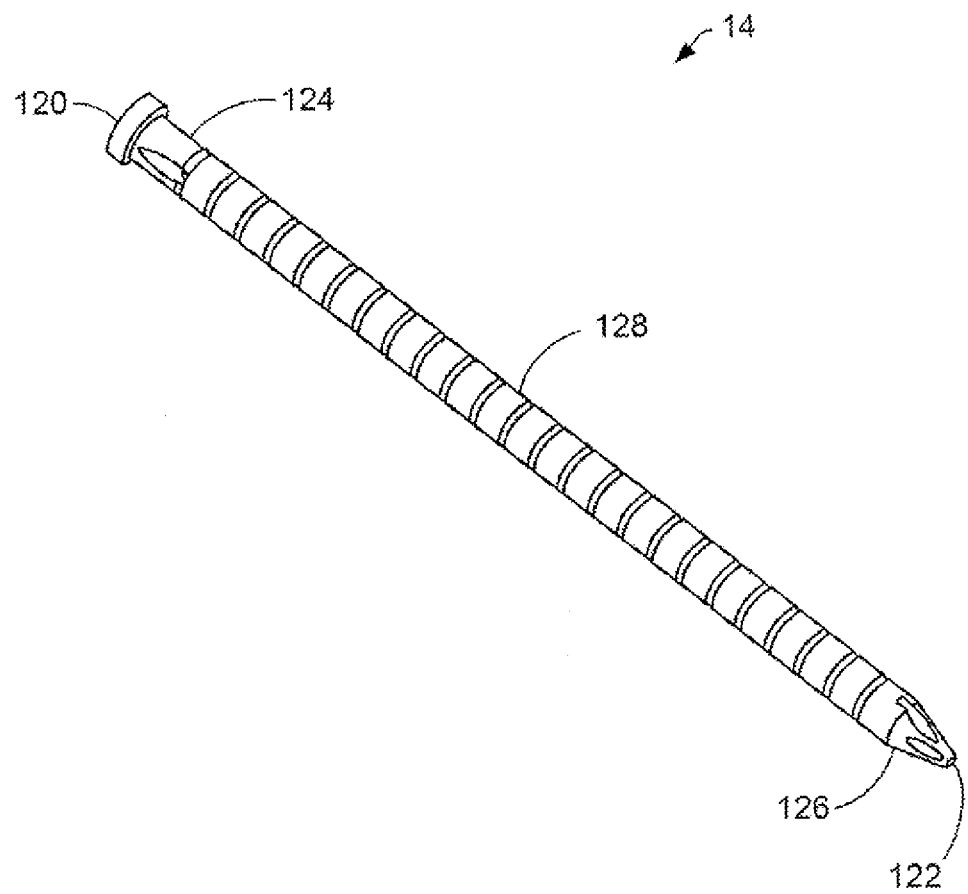
FIG. 6 illustrates various embodiments of a sleeve mechanism of the device of FIGS. 1A and 1B.

FIG. 6 illustrates various embodiments of the second mechanism 14 of the device 10. The second mechanism 14 is a multi-linked mechanism and includes a first end 120 and a second end 122. The first end 120 may be considered the proximal end and the second end 122 may be considered the distal end. The second mechanism 14 includes a first link 124, a second link 126, and any number of intermediate links 128 between the first and second links 124, 126. The first link 124 may be considered the proximal link, and the second link 126 may be considered the distal link.

Figure 7A:
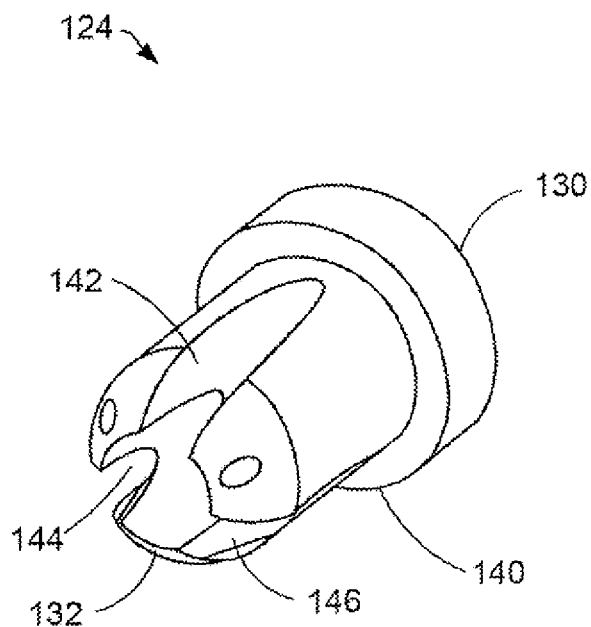
FIGS. 7A-7C illustrate various embodiments of a proximal link of the sleeve mechanism.
Figure 7B:
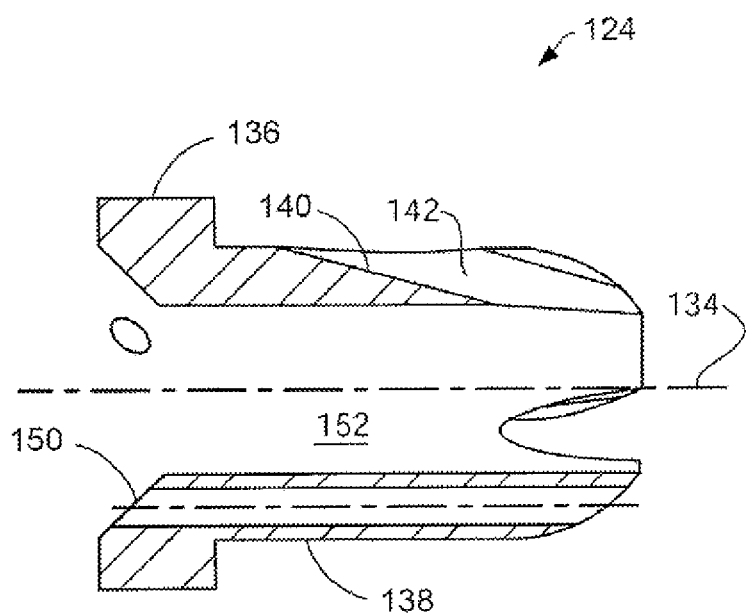
Figure 7C:
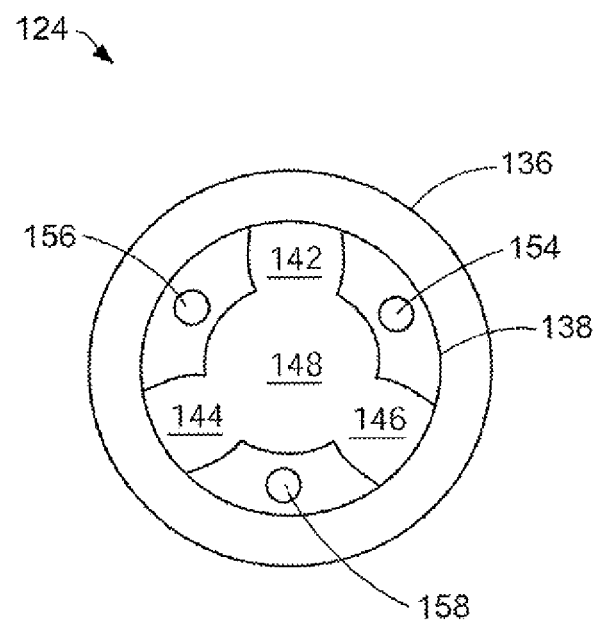

FIGS. 7A-7C illustrate various embodiments of the first link 124 (outer proximal link) of the second mechanism 14. The first link 124 includes a first end 130 and a second end 132, and defines a longitudinal axis 134 that passes through the center of the first end 130 and the center of the second end 132 as shown in FIG. 7B. The first link 124 may be fabricated from any suitable material. According to various embodiments, the first link 124 is fabricated from a stainless steel material such as, for example, 316 stainless steel. The first link 124 has a generally bullet-shaped exterior and is described in more detail hereinbelow.

The first link 124 includes a first portion 136 and a second portion 138. The first portion 136 may be considered the proximal portion and the second portion 138 may be considered the distal portion. The first portion 136 may be fabricated integral with the second portion 138. The first portion 136 has a cylindrical shaped exterior, and extends from the first end 130 of the first link 124 toward the second end 132 of the first link 124. According to various embodiments, the diameter of the first portion 136 is on the order of approximately 12.70 millimeters.

The second portion 138 has a generally cylindrically shaped exterior. The second portion 138 has a cylindrically shaped exterior where it contacts the first portion 136, and tapers toward the second end 132 of the first link 124. The second portion 138 may be shaped in the form of a generally segmented hemisphere at the second end 132 of the first link 124. According to various embodiments, the diameter of the second portion 138 is on the order of approximately 9.50 millimeters where it contacts the first portion 136.

The second portion 138 includes a first surface 140. The first surface 140 may be considered the outer surface of the second portion 138. The second portion 138 defines a first groove 142 along the first surface 140, a second groove 144 along the first surface 140, and a third groove 146 along the first surface 140. Each of the first, second and third grooves 142, 144, 146 are oblique relative to the longitudinal axis 134 and extend along the first surface 140 toward the second end 132 of the first link 124. According to various embodiments, each of the grooves 142, 144, 146 are oriented at an angle on the order of approximately 15° relative to the longitudinal axis 134. As shown in FIG. 7C, the first, second and third grooves 142, 144, 146 may be evenly spaced about the first surface 140 of the first link 124. According to various embodiments, the first, second, and third grooves 142, 144, 146 may be configured in the shape of a segmented cylinder. The size of each of the grooves 142, 144, 146 may identical to one another or may be different from one another. For example, according to various embodiments, each of the grooves 142, 144, 146 are configured as segments of respective cylinders having diameters on the order of approximately 3.0 millimeters. The first, second and third grooves 142, 144, 146 are each configured to facilitate the introduction various tools or instruments (e.g., ablation tools) into the multi-linked device 10. The length of the first link 124 may be on the order of approximately 18.5 millimeters. However, one skilled in the art will appreciate that the length of the first link 124 can vary based on the application.

The first link 124 also defines a passage 148 extending from the first end 130 to the second end 132 along the longitudinal axis 134 as shown in FIG. 7B. The passage 148 is of a size sufficient to allow the first mechanism 12 to pass therethrough. According to various embodiments, the passage 148 is generally configured as a complex shape that includes a combination of a segmented cone 150 that extends from the first end 130 toward the second end 132, and a cylinder 152 that extends from the segmented cone 150 to the second end 132 of the first link 124. According to various embodiments, the segmented cone 150 has a diameter on the order of approximately 7.0 millimeters at the first end 130 of the first link 124, and is tapered at an angle on the order of approximately 45° relative to the longitudinal axis 134. The cylinder 152 has a diameter on the order of approximately 5.50 millimeters.

The first link 124 also defines a first through-hole 154, a second through-hole 156, and a third through-hole 158. (See FIG. 7C). The first through-hole 154 is substantially parallel to the longitudinal axis 134, extends from the first portion 136 toward the second end 132, and is positioned between the passage 148 and the first surface 140. The second through-hole 156 is substantially parallel to the longitudinal axis 134, extends from the first portion 136 to the second end 132, and is positioned between the passage 148 and the first surface 140. The third through-hole 158 is substantially parallel to the longitudinal axis 134, extends from the first portion 136 to the second end 132, and is positioned between the passage 148 and the first surface 140. The first, second and third through-holes 154, 156, 158 are generally cylindrically shaped. According to various embodiments, the through-holes 154, 156, 158 are evenly spaced from one another as shown in FIG. 7C. The size of each of the through-holes 154, 156, 158 may be identical to one another or may be different from one another. For example, according to various embodiments, the respective diameters associated with the through-holes 154, 156, 158 may each be on the order of approximately 1.20 millimeters. The first through-hole 154 is configured to receive and surround the first cable 16. The second through-hole 156 is configured to receive and surround the second cable 18. The third through-hole 158 is configured to receive and surround the third cable 20. The first, second and third through-holes 154, 156, 158 may serve as guidepaths for movement of the first, second and third cables 16, 18, 20.

Figure 8A:
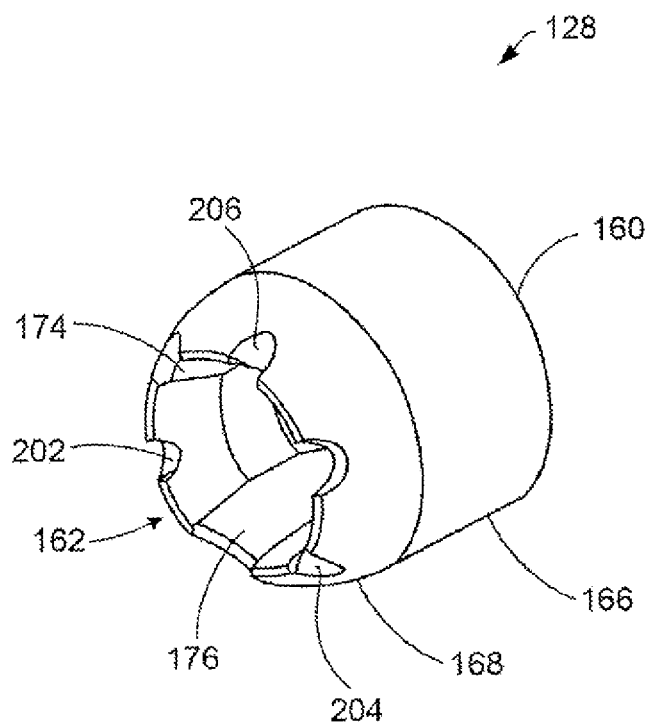
FIGS. 8A-8C illustrate various embodiments of an intermediate link of the sleeve mechanism.
Figure 8B:
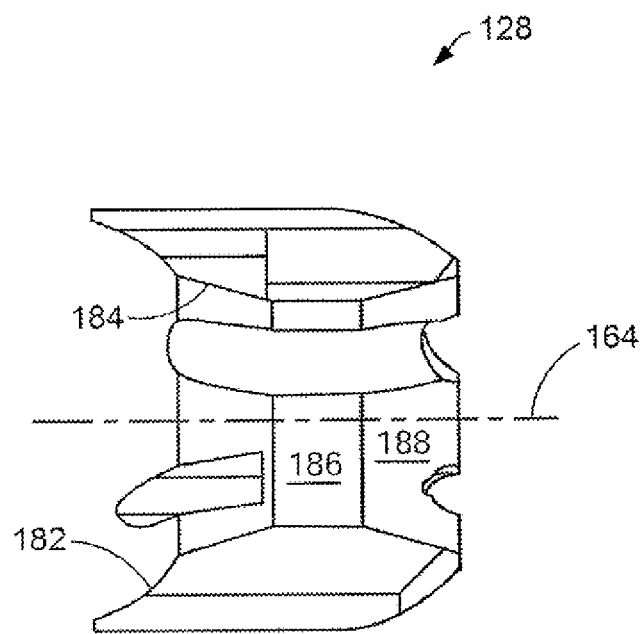
Figure 8C:
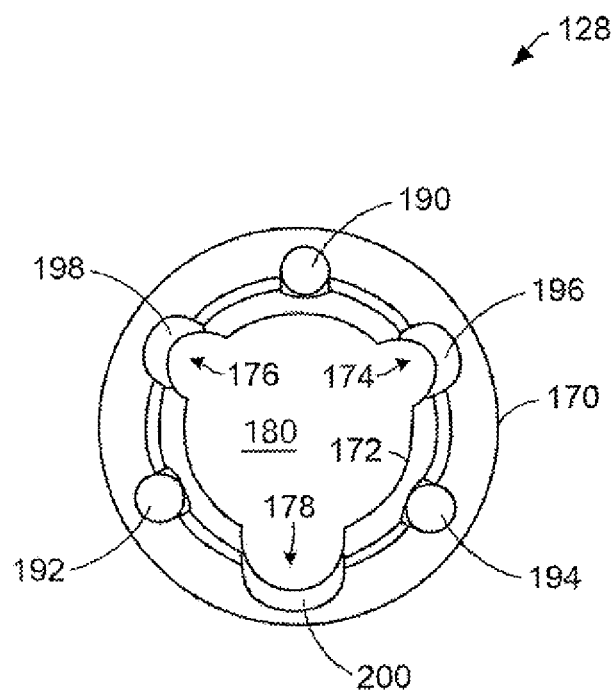

FIGS. 8A-8C illustrate various embodiments of one of the intermediate links 128 (outer intermediate link) of the second mechanism 14. The intermediate link 128 is representative of the other intermediate links 128. The intermediate link 128 includes a first end 160 and a second end 162, and defines a longitudinal axis 164 that passes through the center of the first end 160 and the center of the second end 162 as shown in FIG. 8B. The intermediate link 128 may be fabricated from any suitable material. According to various embodiments, the intermediate link 128 is fabricated from a polymer thermoplastic material such as, for example, polysulfone. The intermediate link 128 has a generally bullet-shaped exterior and is described in more detail hereinbelow.

The intermediate link 128 includes a first portion 166 and a second portion 168. The first portion 166 may be considered the proximal portion and the second portion 168 may be considered the distal portion. The first portion 166 may be fabricated integral with the second portion 168. The first portion 166 has a generally cylindrical shaped exterior, and extends from the first end 160 of the intermediate link 128 toward the second end 162 of the intermediate link 128. According to various embodiments, the second portion 168 has a generally cylindrically shaped exterior where it contacts the first portion 166, and tapers toward the second end 162 of the intermediate link 128. The exterior of the second portion 168 is configured in the form of a generally segmented hemisphere. According to various embodiments, the diameter of the intermediate link 128 is on the order of approximately 9.65 millimeters at the first end 160 thereof. The length of the intermediate link 128 may be on the order of approximately 8.40 millimeters. However, one skilled in the art will appreciate that the length of the intermediate link 128 can vary based on the application.

The intermediate link 128 also includes a first surface 170 that extends from the first end 160 of the intermediate link 128 to the second end 162 of the intermediate link 128, and a second surface 170 that extends from the first end 160 of the intermediate link 128 to the second end 162 of the intermediate link 128. The first surface 170 may be considered the outer surface of the intermediate link 128, and the second surface 172 may be considered the inner surface of the intermediate link 128. The intermediate link 32 also defines a first groove 174 substantially parallel to the longitudinal axis 164 along the second surface 172, a second groove 176 substantially parallel to the longitudinal axis 164 along the second surface 172, and a third groove 178 substantially parallel to the longitudinal axis 164 along the second surface 172. Each of the first, second and third grooves 174, 176, 178 extend along the second surface 172 toward the second end 162 of the intermediate link 128. The first, second and third grooves 174, 176, 178 may be semi-tubular shaped and may be evenly spaced about the second surface 172 of the intermediate link 128 as shown in FIG. 8C. According to various embodiments, the first, second, and third grooves 174, 176, 178 may be configured in the shape of a segmented cylinder. The size of each of the grooves 174, 176, 178 may identical to one another or may be different from one another. For example, according to various embodiments, the first and second grooves 174, 176 are configured as segments of cylinders having diameters on the order of approximately 1.75 millimeters at the first end 160 of the intermediate link 128, and the third groove 178 is configured as a segment of a cylinder having a diameter on the order of approximately 2.50 millimeters at the first end 160 of the intermediate link 128. The first, second and third grooves 174, 176, 178 are each configured to receive and partially surround any of a variety of tools or instruments (e.g., ablation tools) which may pass from the first end 24 of the multi-linked device 10 to the second end 26 of the multi-linked device 10.

The intermediate link 128 also defines a passage 180 extending from the first end 160 to the second end 162 along the longitudinal axis 164 as shown in FIG. 8B. The passage 180 is of a size sufficient to allow the first mechanism 12 to pass therethrough. According to various embodiments, the passage 180 is generally configured as a complex shape that includes a combination of a segmented hemisphere 182 that extends from the first end 160 toward the second end 162, a first segmented cone 184 that extends from the segmented hemisphere 182 toward the second end 162, a cylinder 186 that extends from the first segmented cone 184 toward the second end 162, and a second segmented cone 188 that extends from the cylinder 186 to the second end 162 of the intermediate link 128. According to various embodiments, the segmented hemisphere 182 represents a portion of a sphere having a diameter on the order of approximately 9.65 millimeters, the first segmented cone 184 is tapered at an angle on the order of approximately 15° relative to the longitudinal axis 164, the cylinder 186 has a diameter on the order of approximately 5.50 millimeters, and the second segmented cone 188 is tapered at an angle on the order of approximately 15° relative to the longitudinal axis 164. The segmented hemisphere 182 of the passage 180 is configured to receive the second end 132 of the first link 124 when the first link 124 is coupled to the intermediate link 128. Similarly, for a given intermediate link 128, the segmented hemisphere 182 of the passage 180 is configured to receive the second end 162 of another intermediate link 128 when the other intermediate link 128 is coupled to the given intermediate link 128.

The intermediate link 128 also defines a first through-hole 190, a second through-hole 192, and a third through-hole 194. (See FIG. 8C). The first through-hole 190 is substantially parallel to the longitudinal axis 164, extends from the first portion 166 toward the second end 162, and is positioned between the passage 180 and the first surface 170. The second through-hole 192 is substantially parallel to the longitudinal axis 164, extends from the first portion 166 to the second end 162, and is positioned between the passage 180 and the first surface 170. The third through-hole 194 is substantially parallel to the longitudinal axis 164, extends from the first portion 166 to the second end 162, and is positioned between the passage 180 and the first surface 170. The first, second and third through-holes 190, 192, 194 are generally cylindrically shaped. According to various embodiments, the through-holes 190, 192, 194 are evenly spaced from one another. The size of each of the through-holes 190, 192, 194 may be identical to one another or may be different from one another. For example, according to various embodiments, the respective diameters associated with the through-holes 190, 192, 194 may each be on the order of approximately 1.25 millimeters. The first through-hole 190 is configured to receive and surround the first cable 16. The second through-hole 192 is configured to receive and surround the second cable 18. The third through-hole 194 is configured to receive and surround the third cable 20. The first, second and third through-holes 190, 192, 194 may serve as guidepaths for movement of the first, second and third cables 16, 18, 20.

As shown in FIG. 8C, the intermediate link 128 also defines first, second and third indents 196, 198, 200 at the second end 162 thereof resulting, in part, from the combination of the taper associated with the second portion 168 and the configuration and orientation of the first, second, and third grooves 174, 176, 178. The first, second and third indents 196, 198, 200 may be evenly spaced about the second end 162 of the intermediate link 128 as shown in FIG. 8C. The first, second and third indents 196, 198, 200 may serve to reduce the pinching or binding of various tools or instruments (e.g., ablation tools) when one intermediate link 128 of the second mechanism 14 is moved relative to another intermediate link 128 coupled thereto.

The intermediate link 128 also defines fourth, fifth and sixth indents 202, 204, 206 at the second end 162 thereof resulting from the combination of the taper associated with the second portion 168 and the configuration and orientation of the first, second, and third through-holes 190, 192, 194. The fourth, fifth and sixth indents 202, 204, 206 may be evenly spaced about the second end 162 of the intermediate link 128, and may be evenly spaced from the first, second and third indents 196, 198, 200 as shown in FIG. 8C. The fourth, fifth and sixth indents 202, 204, 206 may serve to reduce the pinching or binding of the first, second and third cables 16, 18, 20 when one intermediate link 128 of the second mechanism 14 is moved relative to another intermediate link 128 coupled thereto.

According to various embodiments, an intermediate link 128 may also define an opening (not shown) that extends from the second surface 172 or from one of the grooves 174, 176, 178 to the first surface 170 of the intermediate link 128. The intermediate link 128 may have any number of such openings, and any number of the intermediate links 128 may have such openings. The opening may be utilized as an exit point for a tool or instrument which may pass from the first end 24 of the multi-linked device 10 toward the second end 26 of the multi-linked device 10. For such embodiments, the respective intermediate link 128 may be positioned proximate the second link 126 of the second mechanism 14. The opening may be oriented at any angle relative to the longitudinal axis 134 of the intermediate link 128. When the first mechanism 12 is removed from the second mechanism 14, and a relatively large tool or instrument is advanced from the first end 120 of the second mechanism 14 to the second end 122 of the second mechanism 14, sufficient room may not exist for a second tool or instrument (e.g., fiber optic cable) to pass through the second end 122 of the second mechanism 14. For such instances, the second tool or instrument may exit through an opening of one of the intermediate links 128.

With the above described structure, the first link 124 may be coupled to the intermediate link 128 by seating the second end 132 of the first link 124 in the segmented hemisphere 182 of the passage 180 of the intermediate link 128. As the convex configuration of the second end 132 of the first link 124 generally corresponds with the concave configuration of the segmented hemisphere 182 of the passage 180 of the intermediate link 128, the first link 124 may be coupled to the intermediate link 128 such that the longitudinal axis 134, the first, second and third grooves 142, 144, 146, and the first, second and third through-holes 154, 156, 158 of the first link 124 are respectively aligned with the longitudinal axis 164, the first, second and third grooves 174, 176, 178, and the first, second and third through-holes 190, 192, 194 of the intermediate link 128. The intermediate link 128 may be moved relative to the first link 124 such that the longitudinal axis 164 of the intermediate link 128 is not aligned with the longitudinal axis 134 of the first link 124. According to various embodiments, the configuration of the first link 124 and the intermediate link 128 allows for the intermediate link 128 to be moved relative to the first link 124 coupled thereto such that the longitudinal axis 134 of the first link 124 and the longitudinal axis 164 of the intermediate link 128 are up to approximately 10° out of alignment with one another. Similarly, one intermediate link 128 may be coupled to another intermediate link 128, and so on, by seating the second end 162 of one intermediate link 128 in the segmented hemisphere 182 of the passage 180 of another intermediate link 128. As the convex configuration of the second end 162 of the intermediate link 128 generally corresponds with the concave configuration of the segmented hemisphere 182 of the passage 180 of the intermediate link 128, the intermediate links 128 may be coupled such that the respective longitudinal axes 164, the respective first, second and third grooves 174, 176, 178, and the respective first, second and third through-holes 190, 192, 194 of the intermediate links 128 are aligned. The coupled intermediate links 128 may be moved relative to one another such that the respective longitudinal axes 164 of the coupled intermediate links 128 are not aligned. According to various embodiments, the configuration of the coupled intermediate links 128 allows for one intermediate link 128 to be moved relative to another intermediate link 128 coupled thereto such that the respective longitudinal axes 164 are up to approximately 10° out of alignment with one another.

Figure 9A:
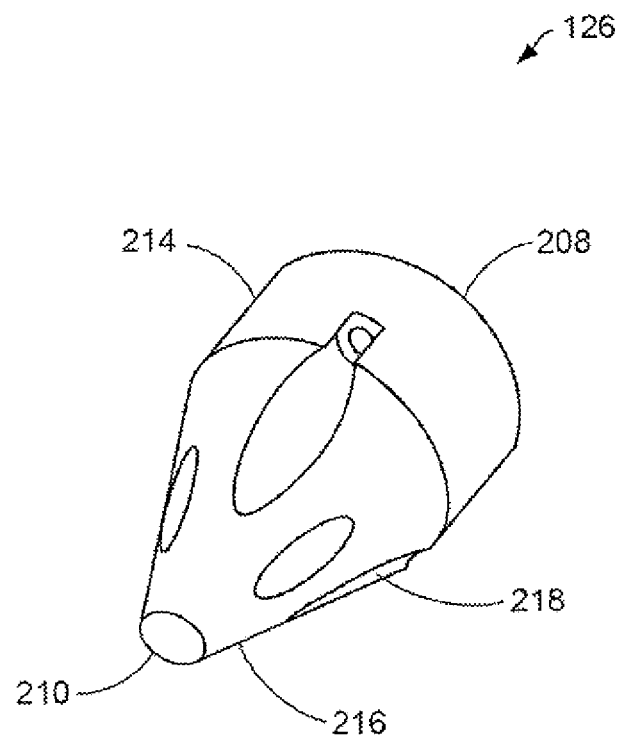
FIGS. 9A-9D illustrate various embodiments of a distal link of the sleeve mechanism.
Figure 9B:
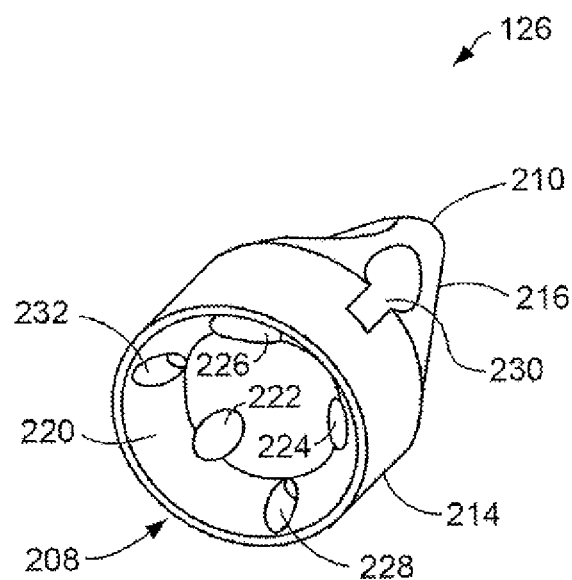
Figure 9C:
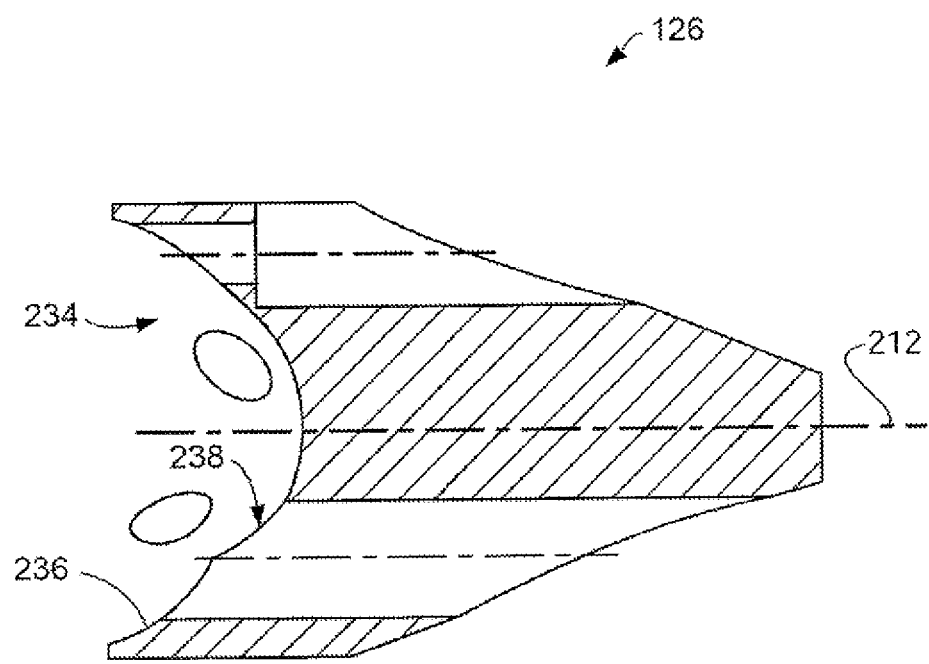

FIGS. 9A-9D illustrate various embodiments of the second link 126 (outer distal link) of the second mechanism 14. The second link 126 includes a first end 208 and a second end 210, and defines a longitudinal axis 212 that passes through the center of the first end 208 and the center of the second end 210 as shown in FIG. 9C. The second link 126 may be fabricated from any suitable material. According to various embodiments, the second link 126 is fabricated from a thermoplastic material such as, for example, Delrin®.

The second link 126 includes a first portion 214 and a second portion 216. The first portion 214 may be considered the proximal portion and the second portion 216 may be considered the distal portion. The first portion 214 may be fabricated integral with the second portion 216. The first portion 214 has a generally cylindrical shaped exterior, and extends from the first end 208 of the second link 126 toward the second end 210 of the second link 126. According to various embodiments, the diameter of the first portion 214 is on the order of approximately 4.80 millimeters.

According to various embodiments, the second portion 216 has a generally cylindrically shaped exterior where it contacts the first portion 214, and tapers toward the second end 210 of the second link 126. The exterior of the second portion 216 is configured in the form of a generally segmented cone. According to various embodiments, the exterior of the second portion 216 tapers from the first portion 214 to the second end 210 of the second link 126 at an angle on the order of approximately 20° relative to the exterior of the first portion 214. The length of the second link 126 may be on the order of approximately 15 millimeters. However, one skilled in the art will appreciate that the length of the second link 126 can vary based on the application.

The second link 126 also includes a first surface 218 that extends from the first end 208 of the second link 126 to the second end 210 of the second link 126, and a second surface 220 that extends from the first end 208 of the second link 126 toward the second end 210 of the second link 126. The first surface 218 may be considered the outer surface of the second link 126, and the second surface 220 may be considered the inner surface of the second link 126.

Figure 9D:
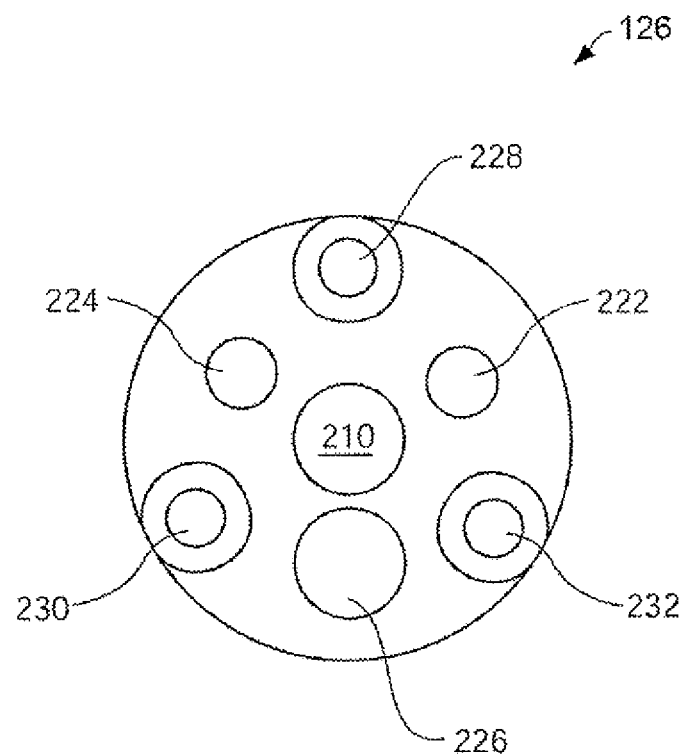

The second link 126 also defines a first port 222, a second port 224, and a third port 226. (See FIG. 9B). The first port 222 extends from the second surface 220 to the first surface 218 and is substantially parallel to the longitudinal axis 212. The second port 224 extends from the second surface 220 to the first surface 218 and is substantially parallel to the longitudinal axis 212. The third port 226 extends from the second surface 220 to the first surface 218 and is substantially parallel to the longitudinal axis 212. The first, second and third ports 222, 224, 226 may be cylindrical shaped and may be evenly spaced about the longitudinal axis 212 of the second link 126 as shown in FIG. 9D. The size of each of the ports 222, 224, 226 may identical to one another or may be different from one another. For example, according to various embodiments, the first and second ports 222, 224 are configured as cylinders having diameters on the order of approximately 1.50 millimeters, and the third port 226 is configured as a cylinder having a diameter on the order of approximately 2.50 millimeters. The first, second and third ports 222, 224, 226 are each configured to receive and surround any of a variety of tools or instruments (e.g., ablation tools) which may pass from the first end 24 of the multi-linked device 10 to the second end 26 of the multi-linked device 10.

The second link 126 also defines a first through-hole 228, a second through-hole 230, and a third through-hole 232. (See FIG. 9B). The first through-hole 228 extends from the second surface 220 to the first surface 218 and is substantially parallel to the longitudinal axis 212. The second through-hole 230 extends from the second surface 220 to the first surface 218 and is substantially parallel to the longitudinal axis 212. The third through-hole 232 extends from the second surface 220 to the first surface 218 and is substantially parallel to the longitudinal axis 212. The first, second and third through-holes 228, 230, 232 are generally cylindrically shaped. According to various embodiments, the through-holes 228, 230, 232 are evenly spaced from one another as shown in FIG. 9D. The size of each of the through-holes 228, 230, 232 may be identical to one another or may be different from one another. For example, according to various embodiments, the respective diameters associated with the through-holes 228, 230, 232 may each be on the order of approximately 1.25 millimeters. The first through-hole 228 is configured to receive and surround the first cable 16. The second through-hole 230 is configured to receive and surround the second cable 18. The third through-hole 232 is configured to receive and surround the third cable 20. As shown in FIG. 9D, each of the through-holes 228, 230, 232 may comprise a respective counter-bored section 228a, 230a, 232a at the distal end of the through-holes 228, 230, 232.

The second link 126 also defines a recess 234 that extends from the first end 208 toward the second end 210 along the longitudinal axis 212 as shown in FIG. 9C. According to various embodiments, the recess 234 is generally configured as a complex shape that includes a combination of a first segmented hemisphere 236 that extends from the first end 208 toward the second end 210, and a second segmented hemisphere 238 that extends from the first segmented hemisphere 236 toward the second end 210 of the second link 126. According to various embodiments, the first segmented hemisphere 236 represents a portion of a sphere having a diameter on the order of approximately 9.50 millimeters, and second segmented hemisphere 238 represents a portion of a sphere having a diameter on the order of approximately 7.0 millimeters. The first segmented hemisphere 236 of the recess 234 is configured to receive the second end 162 of an intermediate link 128 when the intermediate link 128 is coupled to the second link 126.

With the above described structure, an intermediate link 128 may be coupled to the second link 126 by seating the second end 162 of the intermediate link 128 in the first segmented hemisphere 236 of the recess 234 of the second link 126. As the convex configuration of the second end 162 of the intermediate link 128 generally corresponds with the concave configuration of the first segmented hemisphere 236 of the recess 234 of the second link 126, the intermediate link 128 may be coupled to the second link 126 such that the longitudinal axis 164, the first, second and third grooves 174, 176, 178, and the first, second and third through-holes 190, 192, 194 of the intermediate link 128 are respectively aligned with the longitudinal axis 212, the first, second and third ports 222, 224, 226, and the first, second and third through-holes 228, 230, 232 of the second link 126. The second link 126 may be moved relative to the intermediate link 128 coupled thereto such that the respective longitudinal axes 164, 212 are not aligned. According to various embodiments, the configuration of the second link 126 allows for an intermediate link 128 coupled thereto to be moved relative to the second link 126 such that the respective longitudinal axes 164, 212 are up to approximately 10° out of alignment with one another.

When the first mechanism 12 is inserted into the second mechanism 14, the first second and third grooves 70, 72, 74 of the intermediate links 32 of the first mechanism 12 may be substantially aligned with the first, second and third grooves 174, 176, 178 of the intermediate links 128 of the second mechanism 14, and the first, second and third grooves 98, 100, 102 of the second link 30 of the first mechanism 12 may be substantially aligned with the first, second and third ports 222, 224, 226 of the second link 126 of the second mechanism 14. The combination of the first grooves 70 of the intermediate links 32 of the first mechanism 12 aligned with the first grooves 174 of the intermediate links 128 of the second mechanism 14 allows the respective first grooves 70, 174 to collectively serve as a first working port that is substantially aligned with the first port 222 of the second link 126 of the second mechanism 14. The first groove 70 may be considered the inner portion of the first working port and the first groove 174 may be considered the outer portion of the first working port.

Similarly, the combination of the second grooves 72 of the intermediate links 32 of the first mechanism 12 aligned with the second grooves 176 of the intermediate links 128 of the second mechanism 14 allows the respective second grooves 72, 176 to collectively serve as a second working port that is substantially aligned with the second port 224 of the second link 126 of the second mechanism 14, and the combination of the third grooves 74 of the intermediate links 32 of the first mechanism 12 aligned with the third grooves 178 of the intermediate links 128 of the second mechanism 14 allows the respective third grooves 74, 178 to collectively serve as a third working port that is substantially aligned with the third port 226 of the second link 126 of the second mechanism 14. The second groove 72 may be considered the inner portion of the second working port and the second groove 176 may be considered the outer portion of the second working port. The third groove 74 may be considered the inner portion of the third working port and the third groove 178 may be considered the outer portion of the third working port. The first, second and third working ports may be utilized to pass various tools or instruments (e.g., ablation tools) from the first end 24 of the multi-linked device 10 to the second end 26 of the multi-linked device 10. For the exemplary sizes described hereinabove, the third working port is larger than the first and second working ports. Accordingly, the third working port may be utilized to carry a particular tool or instrument that is too large to be carried by the first or second working ports.

When the respective grooves 70, 72, 74, 174, 176, 178 of the respective intermediate links 32, 128 are aligned and collectively surround the various tools and instruments, the combination of the grooves 70, 72, 74, 174, 176, 178 and the tools and instruments may serve to limit or prevent the rotation of the first mechanism 12 relative to the second mechanism 14.

As the diameter of the passage 180 of the intermediate link 128 of the second mechanism 14 is larger than the diameter of any portion of the first mechanism 12, a three-dimensional space 240 exists between the first mechanism 12 and the second mechanism 14 when the first mechanism 12 is received by the second mechanism 14 (See FIG. 1B). According to various embodiments, the space 240 may be utilized to carry wiring, tools, instruments, etc. from the first end 24 of the multi-linked device 10 toward the second end 26 of the multi-linked device 10.

The first, second and third cables 16, 18, 20 may be fabricated from any suitable material. For example, according to various embodiments, the cables 16, 18, 20 may be fabricated from a polyethylene fiber cable such as, for example, Spectra®. The cables 16, 18, 20 may be utilized to control the movement of the multi-linked device 10. For example, by applying a substantially equal tension to each of the cables 16, 18, 20, the first mechanism 12 and/or second mechanism 14 may be steered in a direction such that the respective longitudinal axes 38, 62, 90, 134, 164, 212 of each of the links 28, 30, 32, 124, 126, 128 are all aligned. By applying a different tension to one or more of the cables 16, 18, 20, the first mechanism 12 and/or the second mechanism 14 may be steered in a direction such that the respective longitudinal axes 38, 62, 90, 134, 164, 212 of each of the links 28, 30, 32, 124, 126, 128 are not all aligned. The cables 16, 18, 20 may also be utilized to control the relative state of the second mechanism 14. For example, when a uniform tension is applied to the cables 16, 18, 20, the second mechanism 14 is placed in a "rigid" state, and when a tension is removed from the cables 16, 18, 20, the second mechanism 14 is placed in a "limp" state. According to various embodiments, the cables 16, 18, 20 may be attached at the first end 130 of the first link 124 of the second mechanism 14 to respective pullies (not shown) by, for example, respective stopper knots. The cables 16, 18, 20 may be attached to the second end 132 of the second link 126 of the second mechanism 14 by, for example, respective stopper knots positioned in the counter-bore sections 228a, 230a, 232a of the second link 126. One skilled in the art will appreciate that, according to other embodiments, the "rigid" and "limp" states may be achieved by subjecting the first and/or second mechanisms 12, 14 to a twisting force, or by any other manner known in the art.

The fourth cable 22 may be fabricated from any suitable material. For example, according to various embodiments, the cable 22 may be fabricated from a polyethylene fiber cable such as, for example, Spectra®. The fourth cable 22 may be utilized to control the relative state of the first mechanism 12. For example, when the fourth cable 22 is drawn tight, the first mechanism 12 is placed in a "rigid" state, whereas when the fourth cable 22 is let loose, the first mechanism 12 is placed in a "limp" state. According to various embodiments, the fourth cable 22 may be attached at the first end 34 of the first link 28 of the first mechanism 12 to a pully (not shown) by, for example, a stopper knot. The fourth cable 22 may be attached to the second end 88 of the second link 30 of the first mechanism 12 by, for example, a stopper knot.

Figure 10:
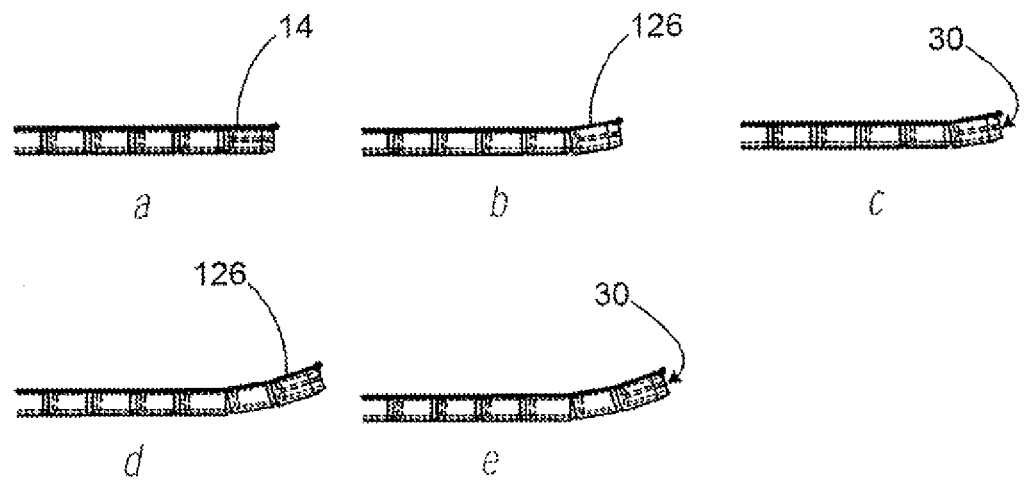
FIG. 10 illustrates various embodiments of a motion sequence of the device of FIGS. 1A and 1B.

FIG. 10 illustrates various embodiments of a motion sequence of the steerable multi-linked device 10. At the start of the sequence, the second mechanism 14 surrounds the first mechanism 12 as shown in step "a" of FIG. 10, the longitudinal axes 38, 62, 90 of the links 28, 30, 32 of the first mechanism 12 are substantially aligned with the respective longitudinal axes 134, 164, 212 of the links 124, 126, 128 of the second mechanism, and the second end 26 of the first mechanism 12 is at substantially the same position as the second end 122 of the second mechanism 14. The fourth cable is pulled tight, thereby placing the first mechanism 12 in the rigid mode. The cables 16, 18, 20 are not pulled tight, thereby placing the second mechanism 14 in the limp mode.

The second mechanism 14 is then advanced so that its second link 126 is positioned approximately one link ahead of the second end 24 of the first mechanism 12 as shown in step "b" of FIG. 10. The cables 16, 18, 20 may be utilized to orient the second link 126 to a particular orientation, where the longitudinal axis 134 of the first link 124 is no longer aligned with the longitudinal axes 164 of the intermediate links 128 of the second mechanism 14 or the longitudinal axis 90 of the second link 30 of the first mechanism 12. After the second link 126 is in the desired position and orientation, the cables 16, 18, 20 are pulled with identical force in order to place the second mechanism 14 in the rigid mode, thereby preserving the position and orientation of the second mechanism 14.

The pulling force of the fourth cable 22 is then released to place the first mechanism 12 the limp mode. After the first mechanism 12 is placed in the limp mode, the first mechanism 12 is advanced so that its second link 30 is at substantially the same position as the second end 122 of the second mechanism 14 as shown in step "c" of FIG. 10. After the second link 30 of the first mechanism 12 is in the desired position and orientation, the fourth cable 22 is pulled tight to place the first mechanism 12 back in the rigid mode, thereby preserving the position and orientation of the first mechanism 12.

The pulling forces of the cables 16, 18, 20 are then released to place the second mechanism 14 back in the limp mode.

After the second mechanism 14 is placed back in the limp mode, the second mechanism 14 is advanced so that its second link 126 is once again positioned approximately one link ahead of the second end 26 of the first mechanism 12 as shown in step "d" of FIG. 10. After the second link 126 is in the desired position and orientation, the cables 16, 18, 20 are pulled with identical force in order to place the second mechanism 14 in the rigid mode, thereby preserving the position and orientation of the second mechanism 14.

The pulling force of the fourth cable 22 is then released to place the first mechanism 12 back in the limp mode. After the first mechanism 12 is placed back in the limp mode, the first mechanism 12 is advanced so that its second link 30 is once again at substantially the same position as the second end 122 of the second mechanism 14 as shown in step "e" of FIG. 10. After the second link 30 of the first mechanism 12 is in the desired position and orientation, the fourth cable 22 is pulled tight to place the first mechanism 12 back in the rigid mode, thereby preserving the position and orientation of the first mechanism 12. The general motion sequence described hereinabove, may be repeated any number of times, and the second link 126 of the second mechanism 14 may be advancing in any direction and orientation. One skilled in the art will appreciate that any number of motion sequences may be utilized with the multi-linked device 10. For example, according to various embodiments, the second mechanism 14 may advance any number of links ahead of the first mechanism 12.

The exemplary sizes described hereinabove are generally relative to each other, and one skilled in the art will appreciate that the multi-linked device 10 can be scaled up or scaled down. For example, although the diameter at the largest portion of the intermediate link 128 of the multi-linked device 10 is on the order of approximately 9.65 millimeters for the embodiments described hereinabove, one skilled in the art will appreciate that, for other embodiments, the intermediate link 128 can be scaled down such that the diameter at the largest portion of the intermediate link 128 of the multi-linked device 10 is on the order of approximately 1.0 millimeter. For such embodiments, each of the other components of the multi-linked device 10 would also be proportionally scaled down.

Figure 11:
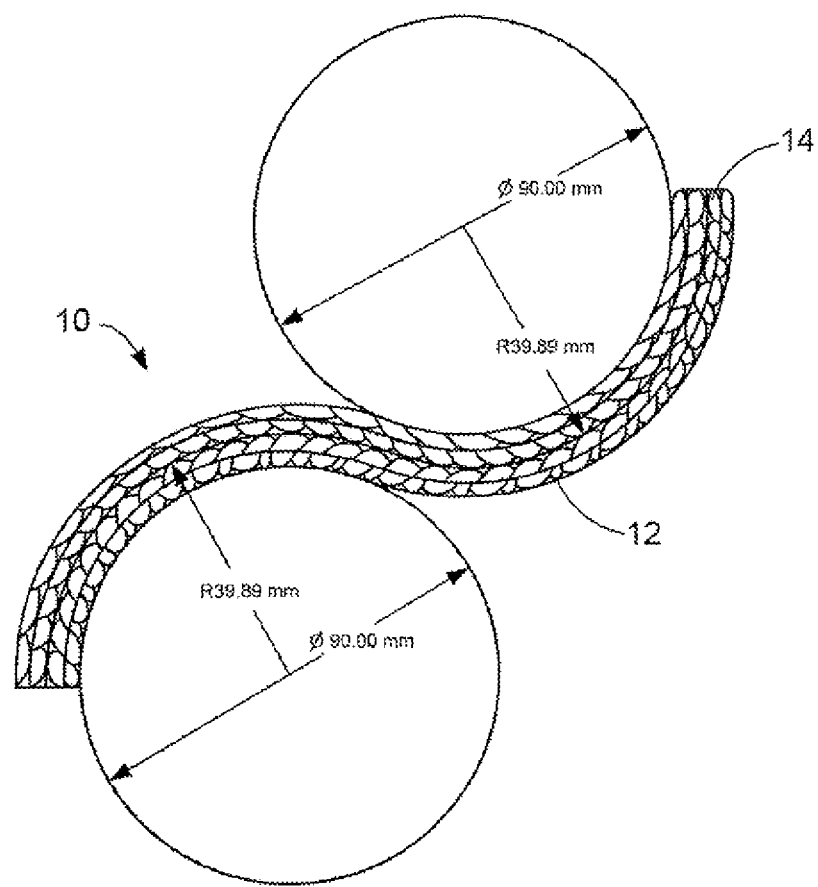
FIG. 11 illustrates various embodiments of a steerable multi-linked device traversing a path having tight curvatures.

The combination of the unique configuration of the respective links 28, 30, 32 which comprise the first mechanism 12 and the unique configuration of the respective links 124, 126, 128 which comprise the second mechanism 14 provides the multi-linked device 10 with the ability to traverse a path defined by the circumference of a circle having a relatively small radius. For example, for the exemplary sizes described hereinabove, the multi-linked device 10 can traverse a path defined by the circumference of a circle having a radius on the order of approximately 40 millimeters. An example of the multi-linked device 10 navigating such tight curvatures is shown in FIG. 11. For embodiments where the outer diameter of the multi-linked device 10 is on the order of approximately 1.0 millimeter, the multi-linked device 10 can traverse a path defined by the circumference of a circle having a radius on the order of approximately 4.0 millimeters. Stated differently, the multi-linked device 10 can traverse a path defined by a circumference of a circle having a radius which is approximately only four times the outer diameter of the device 10. One skilled in the art will appreciate that the ability to navigate such tight curvatures makes the multi-linked device 10 suitable for use in a number of different minimally invasive procedures, both in luminal spaces and in intracavity spaces.

Figure 12:
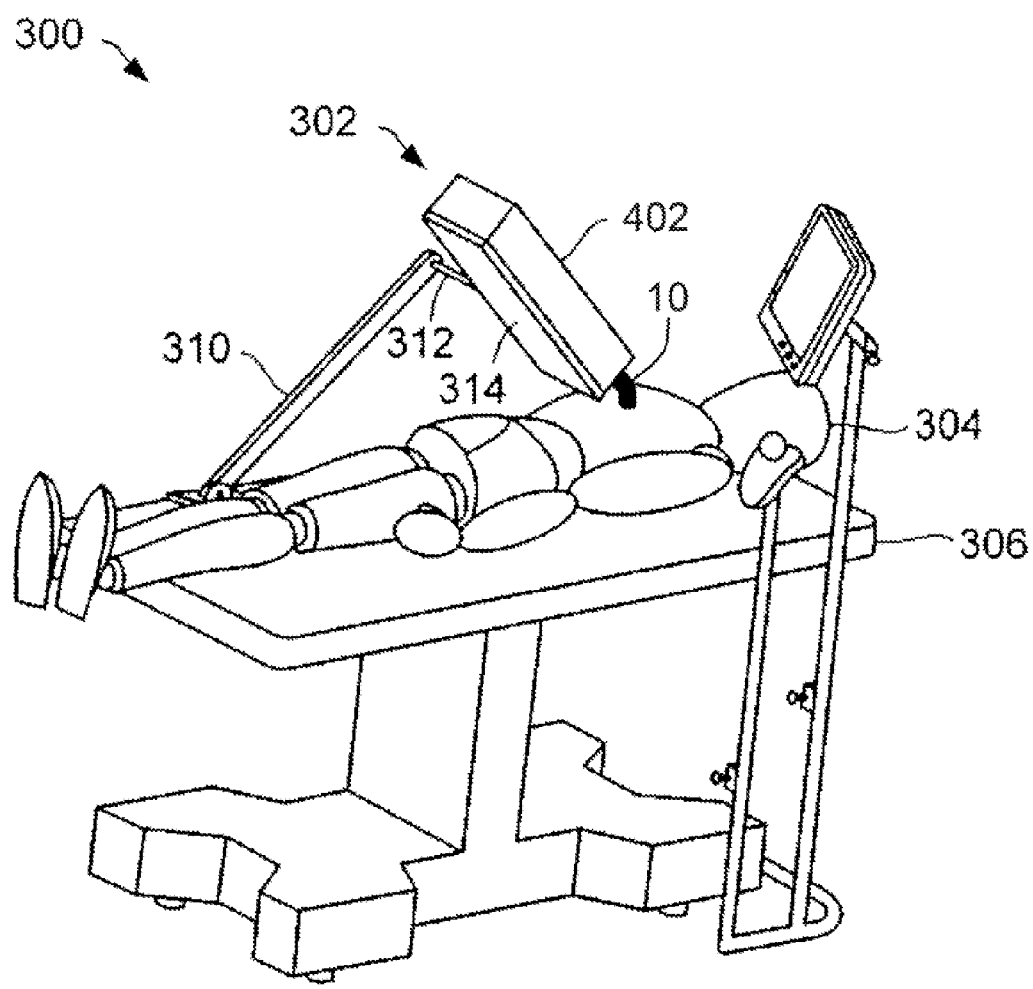
FIG. 12 illustrates various embodiments of an apparatus for positioning a device.

FIG. 12 illustrates various embodiments of an apparatus 300 for positioning a device 302. The device 302 may be any type of device which can be utilized for applications involving surgery, surveillance, inspection, etc. With respect to surgery applications, the device 302 may comprise a feeder that may be utilized to insert or extract the multi-linked device 10 into or from a patient 304 positioned on an operating table 306, and the apparatus 300 may be utilized to position the device 302 relative to the patient 304. For purposes of clarity, the multi-linked device 10 is not shown in FIG. 12. The apparatus 300 includes a first arm 310 and a second arm 312. The second arm 312 is coupled to the first arm 310 and to a support member 314 which is connected to the device 302. The apparatus 300 has at least five degrees of freedom.

FIGS. 13A-13E illustrate various embodiments of an apparatus 400 for positioning a device 402. The device 402 may be any type of device which can be utilized for applications involving surgery, surveillance, inspection, etc. With respect to surgery applications, the device 402 may comprise a feeder that may be utilized to insert or extract the multi-linked device 10 into or from a patient positioned on an operating table, and the apparatus 400 may be utilized to position the device 402 relative to the patient. For purposes of clarity, neither the patient, the operating table, nor the multi-linked device 10 are shown in FIGS. 13A-13E, and certain components of the feeder 402 are not shown. As explained in more detail hereinbelow, the apparatus 400 has at least five degrees of freedom.

The apparatus 400 is structured and arranged such that the apparatus 400 and the device 402 do not interfere with personnel working on the patient. The apparatus 400 includes a first arm 410, a second arm 412, a coupling member 414, and a sloped support member 416.

The first arm 410 may be of any suitable size and shape. According to various embodiments, the first arm 410 may have a cylindrical shape, a rectangular shape, etc., and may have a length on the order of approximately three to four feet. The first arm 410 may be fabricated from any suitable material. For example, according to various embodiments, the first arm 410 is fabricated from a metal such as, for example, aluminum. According to other embodiments, the first arm 410 is fabricated from a plastic. In various implementations, the first arm 410 is coupled to an operating table in a manner similar to that shown in FIG. 12. The first arm 410 may be coupled to the operating table in any suitable manner. For example, according to various embodiments, the first arm 410 may be coupled to the operating table via a bracket mounted to the operating table, via a universal mount, via a pivot joint, etc. For embodiments where the first arm 410 is coupled to the operating table via a pivot joint, the angle of the first arm 410 relative to a top surface of the operating table may be varied, either manually or by a control system 444. In other implementations, the first arm 410 is mounted to a moveable base which is not connected to the operating table.

The second arm 412 may be of any suitable size and shape. According to various embodiments, the second arm 412 may have a cylindrical shape, a rectangular shape, etc. The second arm 412 may be fabricated from any suitable material. For example, according to various embodiments, the second arm 412 is fabricated from a metal such as, for example, aluminum. According to other embodiments, the second arm 412 is fabricated from a plastic. The second arm 412 is coupled to the first arm 410 via the coupling member 414. According to various embodiments, the second arm 412 includes a first portion 418 which is a fixed portion and a second portion 420 which is a movable (e.g., telescopic) portion. The second portion 420 is movable relative to the first portion 418. The position of the second portion 420 relative to the first portion 418 may be varied either manually or by a control system 444.

According to various embodiments, a given position of the second portion 420 relative to the first portion 418 may be maintained by a fastener such as, for example, a set screw. According to other embodiments, the force of gravity may serve to maintain the position of the second portion 420 relative to the first portion 418. According to yet other embodiments, a given position of the second portion 420 relative to the first portion 418 may be maintained by a motor 442. The second portion 420 may be extended and retracted relative to the first portion 418 such that the maximum effective length of the second arm 412 is on the order of approximately two feet and the minimum effective length of the second arm 412 is on the order of approximately one foot.

Figure 14A:
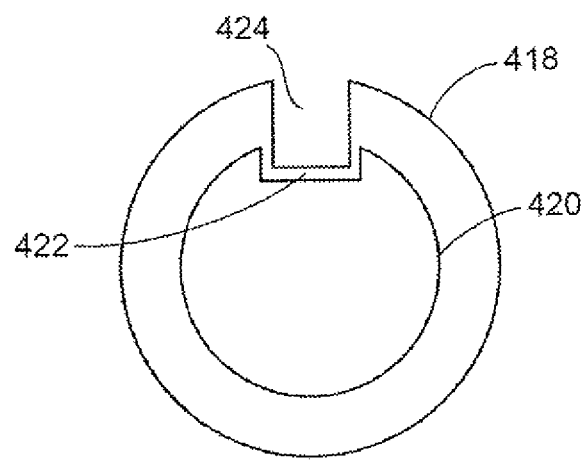
FIGS. 14A and 14B illustrate various embodiments of a fixed portion and a movable portion of an arm of the apparatus of FIGS. 13A-13E.
Figure 14B:
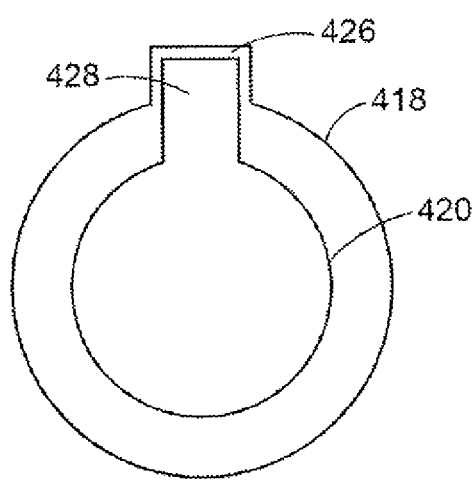

According to various embodiments, as shown in FIG. 14A, the outer surface of the second portion 420 may define a keyway 422, and the inner surface of the first portion 418 may define a protrusion 424 structured and arranged to be received by the keyway 422. According to other embodiments, as shown in FIG. 14B, the inner surface of the first portion 418 may define a keyway 426, and the outer surface of the second portion 420 may define a protrusion 428 structured and arranged to be received by the keyway 426. Such arrangements may serve to prevent the first and second portions 418, 420 from rotating with respect to one another.

Figure 15:
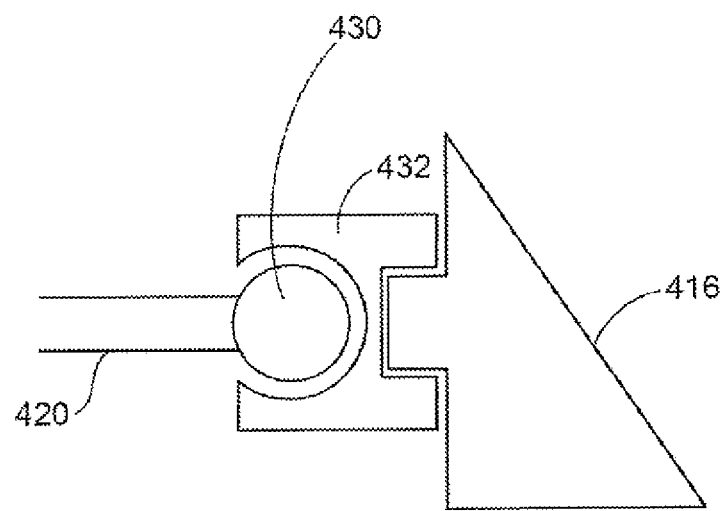
FIG. 15 illustrates various embodiments of a ball, a socket and a sloped support member of the apparatus of FIGS. 13A-13E.

Returning to FIG. 13A, the second arm 412 may also include a ball 430 connected to the movable portion 420 of the second arm 412, and a socket 432 coupled to the ball 430. A simplified representation of the ball 430 and socket 432 is shown in FIG. 15. The ball 430 may be fabricated from any suitable material. For example, according to various embodiments, the ball 430 is fabricated from a metal such as, for example, aluminum. According to various embodiments, the ball 430 may be formed integral with the movable portion 420 of the second arm 412. The socket 432 may be fabricated from any suitable material. For example, according to various embodiments, the socket 432 may be fabricated from a plastic. According to various embodiments, the ball 430 and socket 432 cooperate to provide three degrees of freedom (e.g., pitch, yaw, and roll). According to other embodiments, the socket 432 is a constrained socket, and the ball 430 and socket 432 cooperate to provide at least two degrees of freedom.

The coupling member 414 defines a first opening 434 and a second opening 436. The first opening 434 is sized to receive the first arm 410 which passes therethrough, and the second opening 436 is sized to receive the second arm 412 which therethrough. According to various embodiments, the first and second openings 434, 436 are oriented approximately 90° relative to one another. The coupling member 414 may be fabricated from any suitable material. For example, according to various embodiments, the coupling member 414 is fabricated from a metal such as, for example, aluminum. According to other embodiments, the coupling member 414 is fabricated from a plastic. According to various embodiments, the coupling member 414 may be removably secured to the first arm 410 by, for example, a fastener such as, for example, a set screw. According to various embodiments, a given position of the coupling member 414 relative to the first arm 410 may be maintained by a motor 442.

The coupling member 414 may be rotatably connected to the first arm 410 such that the coupling member 414 may be rotated up to 360° about the first arm 410. Such rotation also operates to rotate the second arm 412 about the first arm 410. The coupling member 414 may also be slidably connected to the first arm 410 such that the coupling member 414 may be moved up and down along the first arm 410 as shown, for example, in FIGS. 13A and 13D. Such vertical movement also operates to move the second arm 412 along the length of the first arm 410. The rotational and/or vertical motion of the coupling member 414 relative to the first arm 410 may be realized manually or by a control system 444.

Figure 16:
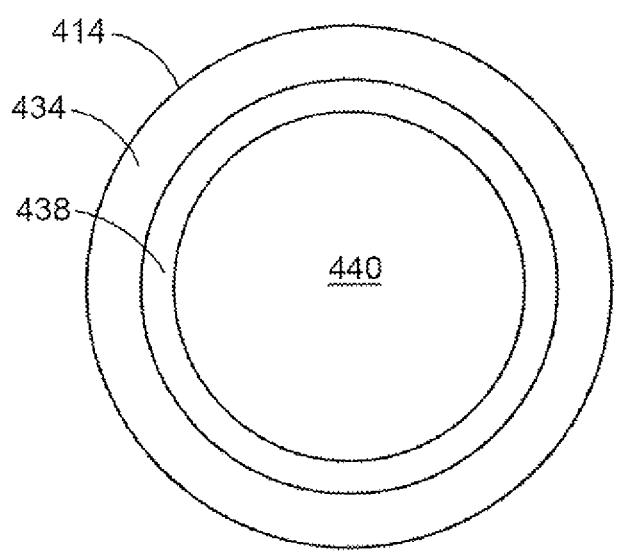
FIG. 16 illustrates various embodiments of a bushing and a coupling member of the apparatus of FIGS. 13A-13E.

According to various embodiments, the apparatus 400 may further comprise a sleeve or bushing 438 positioned in the first opening 434 of the coupling member 414 as shown in FIG. 16. For such embodiments, the first arm 410 passes through an opening 440 defined by the bushing 438, and both the bushing 438 and the coupling member 414 are rotatable about the first arm 410 and are slidable along the first arm 410. According to various embodiments, the coupling member 414 and the bushing 438 are keyed together. For such embodiments, the coupling member 414 and the bushing 438 may be keyed together in a manner similar to the manner in which the first and second portions 418, 420 of the second arm 412 are keyed together as shown in either FIG. 14A or FIG. 14B.

The position of the second arm 412 relative to the coupling member 414 may be fixed, or may be varied either manually or by a control system. According to various embodiments, the coupling member 414 may be removably secured to the second arm 412 by, for example, a fastener such as, for example, a set screw. According to other embodiments, a given position of the coupling member 414 relative to the second arm 412 may be maintained by a motor 442. According to various embodiments, the coupling member 414 and the second arm 412 are keyed together. For such embodiments, the coupling member 414 and the fixed portion 418 of the second arm 412 may be keyed together in a manner similar to the manner in which the first and second portions 418, 420 of the second arm 412 are keyed together as shown in either FIG. 14A or FIG. 14B. Such an arrangement may serve to prevent the fixed portion 418 of the second arm 412 from rotating with respect to the coupling member 414.

Figure 17:
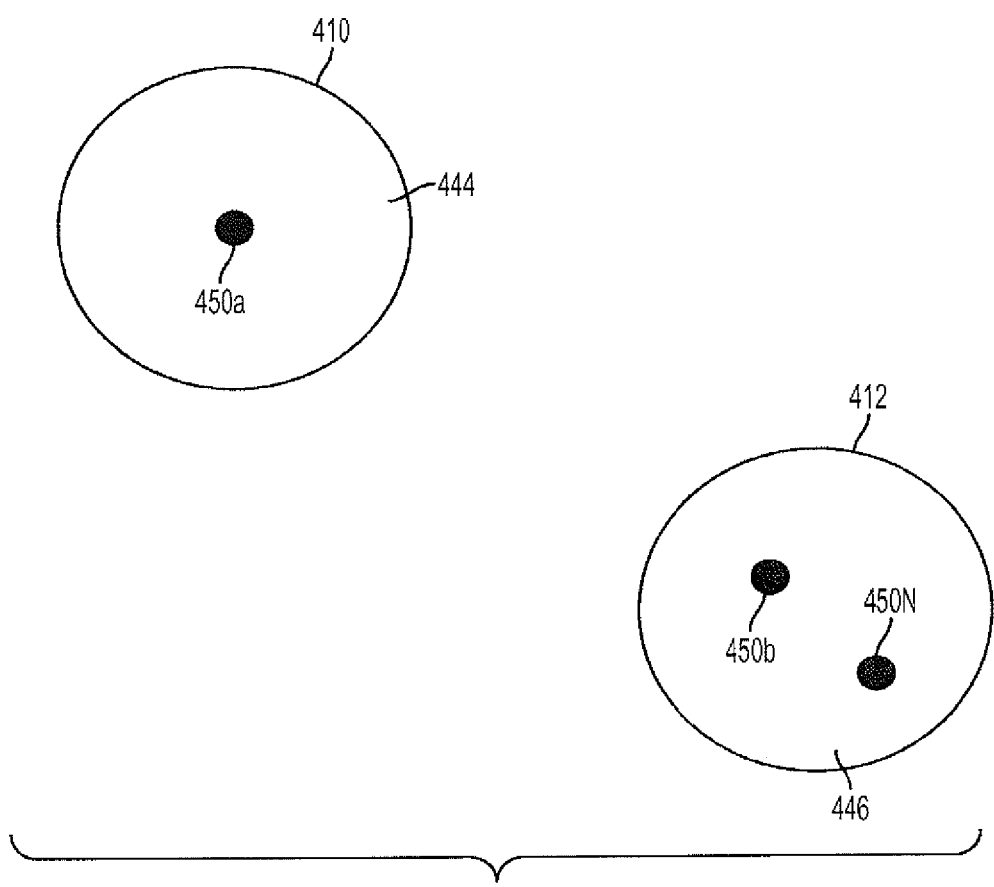
FIG. 17 illustrates various embodiments of a first arm and a second arm.

According to various embodiments, and as illustrated by FIG. 17, each of the first and second arms 410, 412 define hollow areas 446, 448 therein, and power wiring 450a-N and/or control wiring 450a-N may pass through the hollow areas. Such wiring 450a-N may be utilized for the apparatus 400 and/or the feeder 402.

Figure 13A:
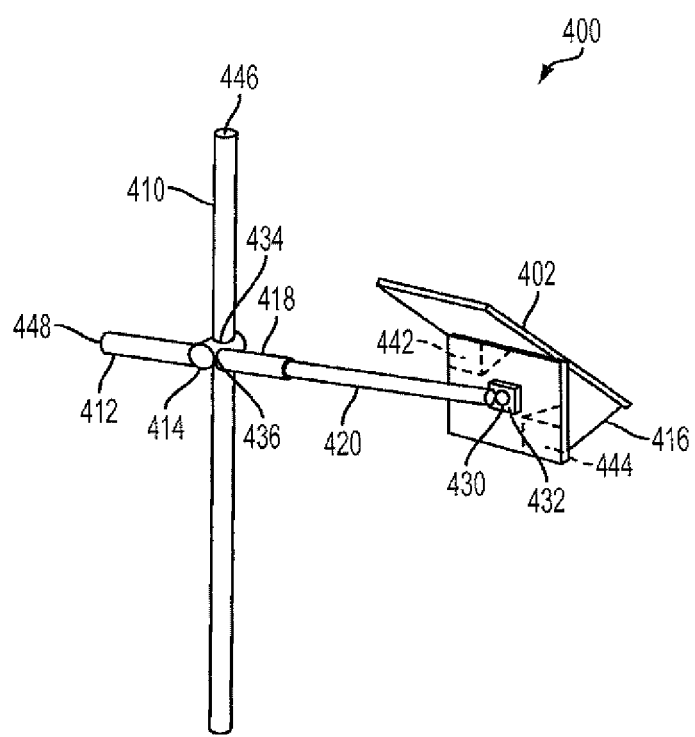
FIGS. 13A-13E illustrate various embodiments of an apparatus for positioning a device.

The sloped support member 416 is releasably connected to the second arm 412. In general, the releasable connection may be realized in any suitable manner. For example, according to various embodiments, the releasable connection is realized by a protrusion of the sloped support member 416 cooperating with a receptacle defined by an end of the second arm 412 as shown, for example, in FIG. 15. According to other embodiments, the releasable connection is realized by a protrusion at an end of the second arm 412 cooperating with a receptacle defined by the sloped support member 416. Such protrusion/receptacle combinations may be considered to be a quick release mechanism due to the relative speed and ease with which the sloped support member 416 can be connected to or disconnected from the second arm 412. As shown in FIG. 13A, the sloped support member 416 may define an angle of approximately 45° relative to a bottom surface of the sloped support member 416. When combined with the functionality of the ball 430 and socket 432, the 45° angle orients a feeder 402 positioned on the sloped support member 416 in an orientation that is useful for minimally invasive surgery over the entire range of motion of the apparatus 400. For other applications, the sloped support member 416 may define an angle that is more than or less than 45° relative to the bottom surface of the sloped support member 416.

Figure 13B:
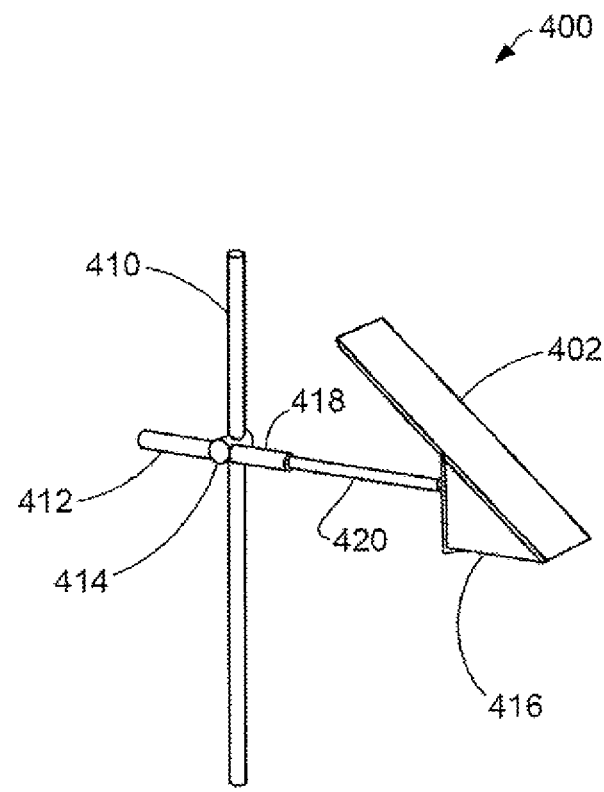
Figure 13C:
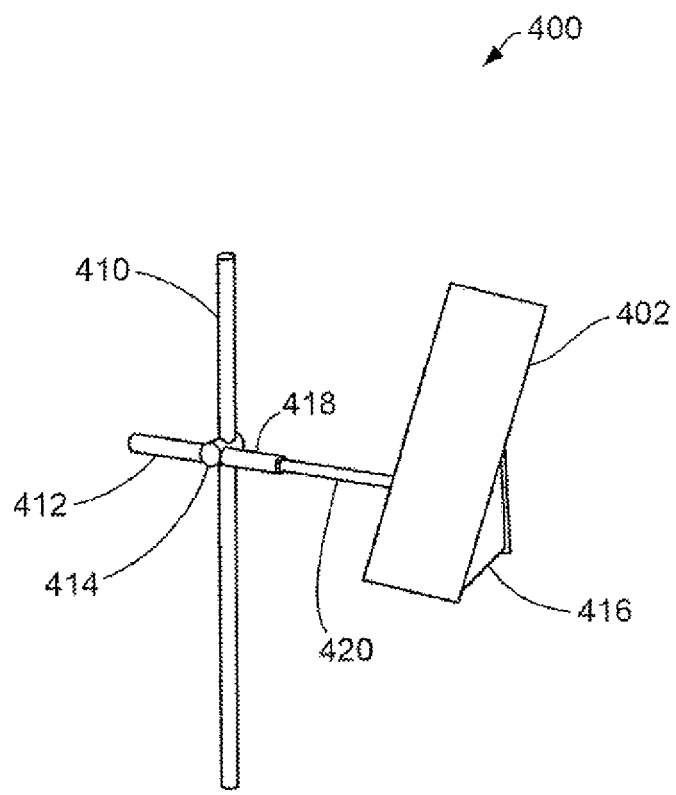
Figure 13D:
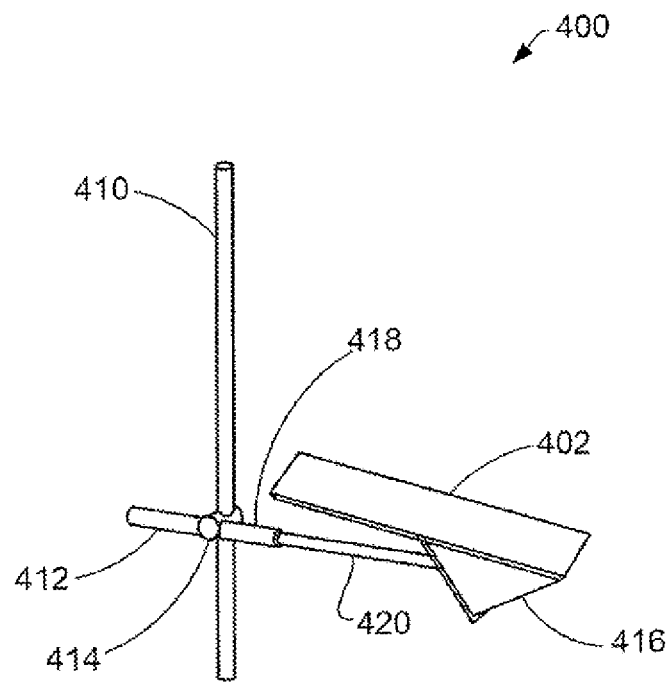
Figure 13E:
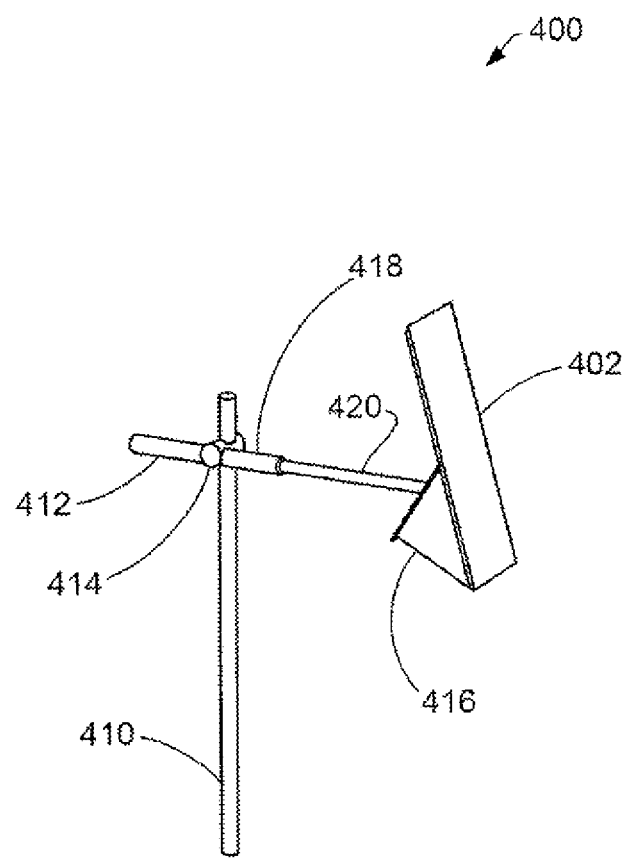

As shown in FIGS. 13A-13E, the structure and arrangement of the ball 430 and socket 432 allows the sloped support member 416 to be moved relative to the movable (e.g., telescopic) portion 420 of the second arm 412. Such movement may be controlled either manually or by a control system. According to various embodiments, the structure and arrangement of the ball 430 and socket 432 allows for pitch and yaw control of the sloped support member 416. For example, as shown in FIGS. 13A-13C, the range of motion about a vertical axis of the movable portion 420 (e.g., yaw) may vary over a range of approximately 180° (+/−)90°, and, as shown in FIGS. 13D-13E, the range of motion about a lateral axis of the movable portion 420 (e.g., pitch) may vary over a range of approximately 40° (+/−)20°. According to other embodiments, the structure and arrangement of the ball 430 and socket 432 may also allow for roll control of the sloped support member 416 about a longitudinal axis of the movable portion 420. As the feeder 402 may be connected to the device support member 416, the ball 430 and socket 432 also allows for pitch and yaw control (and in some embodiments, roll control) of the feeder 402 that may be utilized to insert or extract a multi-linked device 10 into or from a patient.

As described hereinabove, the apparatus 400 may be considered to be a series of serial mechanisms, with each serial mechanism operable to provide a certain number of degrees of freedom. However, those skilled in the art will appreciate that, according to other embodiments, the described functionality of the apparatus 400 may also be realized by replacing at least one of the serial mechanisms with a parallel mechanism. For example, according to various embodiments, the ball 430 and socket 432 may be replaced with a parallel mechanism.

While several embodiments of the invention have been described herein by way of example, those skilled in the art will appreciate that various modifications, alterations, and adaptations to the described embodiments may be realized without departing from the spirit and scope of the invention defined by the appended claims.

What is claimed is:

1. A system for positioning a device, the system comprising:
   a steerable multi-linked device;
   a feeder mechanism connected to at least a portion of the multi-linked device, wherein the feeder mechanism is configured to control movement of the multi-linked device relative to a patient; and
   a positioning apparatus configured to move the feeder mechanism and the multi-linked device with at least three degrees of freedom, wherein the positioning apparatus comprises:
   an arm, and
   a support member that is releasably attached to a portion of the arm, wherein the support member comprises:
   a bottom surface, and
   a top surface that is angled relative to the bottom surface,
   wherein the feeder mechanism is positioned on the top surface.

2. The system of claim 1, wherein the support member is configured to move relative to the arm.

3. The system of claim 2, wherein the support member is configured to move relative to the arm via a control system.

4. The system of claim 2, wherein the arm comprises a ball and a socket.

5. The system of claim 2, wherein a range of motion of the support member about a vertical axis of the arm varies over a range of approximately 180 degrees.

6. The system of claim 2, wherein a range of motion of the support member about a lateral axis of the arm varies over a range of approximately 40 degrees.

7. The system of claim 1, wherein the positioning apparatus has at least five degrees of freedom.

8. The system of claim 1, wherein the arm comprises:
   a first portion, and
   a second portion that is extendible relative to the first portion, wherein the second portion comprises a ball connected to the second portion and a socket coupled to the ball.

9. A system for controlling the movement of a device, the system comprising:
   a steerable multi-linked device;
   a feeder mechanism configured to control movement of the multi-linked device; and
   a positioning apparatus comprising:
   an arm comprising a hollow area, wherein one or more wires connected to one or more of the feeder mechanism and the multi-link device pass through at least a portion of the hollow area, and
   a support member releasable connected to the arm, wherein the support member comprises:
   a bottom surface, and
   a top surface that is angled relative to the bottom surface,
   wherein the feeder mechanism is positioned on the top surface, wherein the support member is configured to move the feeder mechanism and the multi-linked device with at least three degrees of freedom, wherein the positioning apparatus has at least five degrees of freedom.

10. The system of claim 9, wherein the feeder mechanism is configured to perform one or more of the following:
    advance at least a portion of the multi-linked device into a patient; and
    extract at least a portion of the multi-linked device from a patient.

11. The system of claim 9, wherein a range of motion of the support member about a vertical axis of the arm varies over a range of approximately 180 degrees.

12. The system of claim 9, wherein a range of motion of the support member about a lateral axis of the arm varies over a range of approximately 40 degrees.

13. The system of claim 1, wherein the feeder mechanism is configured to advance the steerable multi-linked device.

14. The system of claim 1, wherein the feeder mechanism is configured to extract the steerable multi-linked device.

15. The system of claim 2, wherein the arm comprises a hollow area comprising one or more wires connected to one or more of the feeder mechanism and the multi-linked device.

* * * * *